(12) United States Patent
Miller et al.

(10) Patent No.: US 7,105,707 B2
(45) Date of Patent: Sep. 12, 2006

(54) PROCESS FOR PREPARING ALKYNYL-SUBSTITUTED AROMATIC AND HETEROCYCLIC COMPOUNDS

(75) Inventors: Joseph A. Miller, Greenville, NC (US); Jonathan M. Penney, Greenville, NC (US)

(73) Assignee: PharmaCore, Inc., High Point, NC (US)

( * ) Notice: Subject to any disclaimer, the term of this patent is extended or adjusted under 35 U.S.C. 154(b) by 276 days.

(21) Appl. No.: 10/740,240

(22) Filed: Dec. 17, 2003

(65) Prior Publication Data

US 2005/0137402 A1 Jun. 23, 2005

(51) Int. Cl.
*C07C 41/00* (2006.01)

(52) U.S. Cl. .................. 568/630; 585/400; 570/200; 570/143; 568/658; 549/429; 546/352; 556/466

(58) Field of Classification Search ............... 568/630, 568/658; 585/400; 570/200, 143; 549/429; 546/352; 556/466
See application file for complete search history.

(56) References Cited

U.S. PATENT DOCUMENTS

| | | | |
|---|---|---|---|
| 3,959,220 A | 5/1976 | Hechenbleikner et al. | |
| 4,012,399 A | 3/1977 | Hechenbleikner et al. | |
| 4,263,466 A | 4/1981 | Colon et al. | |
| 4,412,856 A * | 11/1983 | Brunner et al. | 504/326 |
| 4,508,560 A * | 4/1985 | Brunner et al. | 504/251 |
| 4,620,025 A | 10/1986 | Sletzinger et al. | |
| 4,724,260 A * | 2/1988 | Kirchhoff et al. | 546/112 |
| 4,730,032 A | 3/1988 | Rossi et al. | |
| 4,912,276 A | 3/1990 | Puckette | |
| 4,916,227 A | 4/1990 | Puckette | |
| 4,990,647 A | 2/1991 | Himmler et al. | |
| 5,084,204 A * | 1/1992 | Reiffenrath et al. | 252/299.62 |
| 5,128,355 A | 7/1992 | Carini et al. | |
| 5,130,439 A | 7/1992 | Lo et al. | |
| 5,202,349 A | 4/1993 | Zimmer et al. | |
| 5,237,116 A | 8/1993 | Corley et al. | |
| 5,264,456 A * | 11/1993 | Chandraratna | 514/461 |
| 5,288,895 A | 2/1994 | Bouisset et al. | |
| 5,364,943 A | 11/1994 | Rosen et al. | |
| 5,365,007 A | 11/1994 | Wu | |
| 5,532,374 A | 7/1996 | Lee et al. | |
| 5,559,144 A | 9/1996 | Brooks et al. | |
| 5,559,277 A | 9/1996 | Beller et al. | |
| 5,693,728 A | 12/1997 | Okamoto et al. | |
| 5,693,843 A | 12/1997 | Breikss et al. | |
| 5,811,548 A | 9/1998 | Bannwarth et al. | |
| 5,858,907 A | 1/1999 | Wang et al. | |
| 5,874,606 A | 2/1999 | Huang | |
| 5,922,898 A | 7/1999 | Miller et al. | |
| 6,194,599 B1 | 2/2001 | Miller et al. | |
| 6,218,537 B1 | 4/2001 | Adams et al. | |
| 6,252,001 B1 | 6/2001 | Babb et al. | |
| 6,329,526 B1 | 12/2001 | Adams et al. | |
| 6,500,849 B1 * | 12/2002 | Tegeler et al. | 514/357 |
| 6,562,989 B1 | 5/2003 | Hartwig et al. | |
| 6,566,372 B1 * | 5/2003 | Zhi et al. | 514/312 |
| 6,569,871 B1 | 5/2003 | Adams et al. | |
| 2003/0100760 A1 | 5/2003 | Miller | |
| 2005/0010073 A1 | 1/2005 | Dankwardt | |

FOREIGN PATENT DOCUMENTS

| | | |
|---|---|---|
| EP | 0 131 968 | 1/1985 |
| EP | 0 470 794 | 2/1992 |
| EP | 0 470 795 | 2/1992 |

OTHER PUBLICATIONS

Pridgen et al., "New Synthesis of 2-Substituted 2-Oxazolines: Transition-Metal-Catalyzed Cross-Coupling of Grignards with 2-(methylthio)-4, 4-dimethyl- 2oxazoline", J. Org. Chem., 48, 5402-5404, (1981).

Ali et al., "Palladium-Catalysed Cross-Coupling Reactions of Arylboronic Acids with .PI.-Deficient Heteroaryl Chlorides", Tetrahedron, vol. 48, pp. 8117-8126, (1992).

Beletskaya, et al., "The nickel-catalyzed Sonogashira-Hagihara reaction", Tetrahadron Letters, vol. 44, pp. 5011-5013, (2003).

Bleicher and Cosford, "Aryl- and Heleroaryl-alkyne coupling reactions catalyzed by palladium on carbon and CuII in an aqueous medium, " Synlett, 11:1115-1116, (1995).

Bringmann et al., "The Directed Synthesis of Biaryl Compounds: Modern Concepts and Strategies", Angew. Chem. Int. Ed. Engl., vol. 29, 977-991, (1990).

Carini et al., "Nonpeptide Angiotensin II Receptor Antagonists: The Discovery of a Series of N-(Bipheynylymethl)imidazoles as Potent, Orally Active Antihypertensives", J. Med, Chem., vol. 34, pp. 2525-2547, (1991).

Cibulka et al., "Metal Ion Chelates of Lipoophilic Alkyl Diazinyl Ketoximes as Hydrolytic Catalysts", Collect. Czech. Charm. Commun., vol. 64, pp. 1159-1179, (1999).

Clough et al., "Coupling of Nonequivalent Aromatic Rings by Soluble Nickel Catalysts. A General Route to the 1, 8-Diarylnaphthalenes. sub. 1a", J. Org. Chem., vol. 41, pp. 2252-2255, (1976).

Colon et al., "Coupling of Aryl Chlorides by Nickel and Reducing Metals", J. Org. Chem., vol. 51, pp. 2627-2637 (1986).

Diek et al., "Palladium Catalyzed Synthesis of Aryl, Heterocyclic and Vinylic Acelylene Derivatives", Organometallic Chem., 93:529 (1975).

Fuson, R.C. and W.S. Friedlander, "Displacement of substituents in phenyl 2,4,6, -triisoplylphenyl ketone by the action of Grignard reagents", J. Am. Chem. Soc., vol. 75, pp. 5410-5411, (1953).

Fuson, R.C. et al., "The reaction of Grignard reagents with the cyanobenzoyldurenes;", J. Org. Chem., vol. 16, pp. 648-654, (1951).

(Continued)

*Primary Examiner*—Samuel Barts
(74) *Attorney, Agent, or Firm*—Kilpatrick Stockton

(57) ABSTRACT

Mono- and disubstituted aryl or heterocyclic acetylenes are produced by a process comprising reacting an aryl nitrile with an alkynylzinc compound, a bis-alkynylzinc compound, or an alkynylmagnesium compound, in the presence of a nickel/phosphine catalyst.

79 Claims, No Drawings

OTHER PUBLICATIONS

Gorushin et al., "Tranformations of Chloroarenes, Catalyzed by Transition-Metal Complexes", Chem. Rev., vol 94. pp. 1047-1062, (1994).

House et al., "Reactions of the 1,8-Dipenylanthracene System", J. Org. Chem., vol. 45, pp. 1807-1817 (1980).

House et al., "Unsummetrically Substituted 1, 8-Diarlanthracenes", J. Org. Chem., vol. 51, pp. 921-929, (1986).

Kageyama et al., "Nickel-Catalyzed Cross-Coupling Reaction of Aryl Halidas in Pyridine. A Practical Synthesis of 4-Methylbiphenyl-2-carbonitrile As a Key Intermediate of Angiotensine II Receptor Antagonists", Synlett, pp. 371-372, (1994).

Kalinin et al., "Carbon-Carbon Bond Formation in Heterocyclos Using Ni- and Pd-Catalyzed Reactions", Synthesis, pp. 413-432, (1992).

Mantlo et al., "Potent, Orally Active Imidazo 4,5-b pyridine-Based Angiotensin II Receptor Antagonists", J. Med. Chem., vol. 34, pp. 2919-2922 (1991).

Miller and Farrell, "Preparation of unsymmetrical Biaryls via Ni- or Pd-catalyzed coupling of aryl chlorides with aryizincs", Tett.Lett., vol. 39, pp. 6441-6444. (1998).

Miller and Farrell, "Synthesis of functionally substitutedunsymmetriczal Blaryts via a novel double metal catalyzed coupling reaction", Tetrahedron Letters, vol. 39, pp. 7275-7278 (1998).

Miller et al., "Nickel Catalyzed Cross-Coupling and Animation Reactions of Aryl Nitriles", Synthesis. No. 11, pp. 1643-1648, (2003).

Miller et al., "Nickel catalyzed cross-coupling of modified alkyl and alkenyl Grignard reagents with aryl- and Heteroaryl nitriles: activation of the C-CN bond", Tetrahedron Letters, vol. 44, pp. 1907-1910. (2003).

Miller, "C-C Bond Activation with selective functionalization: preparation of unsymmetrical Biaryls for benzonitriles", Tetrahedron Letters, vol. 42, pp. 6991-6993, (2001).

Milner, D.J. et al., "The mono-alkyldecyanation of tetraftuoroterephtatonitrile by reaction with Gringard reagents," J. Organometallic Chem., vol. 302, pp. 147-152, (1986).

Miyaura et al, "The Palladium-Catalyzed Cross-Coupling Reaction of Phenylboronic Acid with Haloarenes in the Presence of Bases", Synthetic Communications, vol. 11, p. 513 (1981).

Nakao, et al., "Nickel-Catalyzed Arylcyanation of Alkynes", Journal American Chemical Society, (2004).

Negishi et al., "Selective Carbon-Carbon Bond Formation via Transition Metal Catalysis, 3. A Highly Selective Synthesis of Unsymmetrical Biaryls and Diarylmethanes by the Nickel- or Palladium-Catalyzed Reaction of Aryl- and Benzylzine Derivatives with Aryl Halides", J. Org. Chem., vol. 42, pp. 1821-1823 (1977).

Penney et al., "Alkynylation of benxonitriles via nickel catalyzed C-C bond activation", vol. 45, pp. 4989-4992, (2004).

Percec et al., "Aryl Mesylales in Metal Catalyzed Homo- and Cross-Coupling Reactions. 4. Scope and Limitations of Aryl Mesylates in Nickel Catalyzed Cross-Coupling Reactions", J. Org. Chem., vol. 60, 6895-6903. (1995).

Pridgen et al, "Oxazolines. 3. Regioselective Synthesis of 2-(Monosubstituted phenyl) and/or Unsymmetrically 2-(Disubstituted phenyl) 2-Oxazolines by Cross-Coupling Grignard Reagents to (Haloaryl)-2-oxazolines", J. Org. Chem., vol. 47, pp. 4319-4323, (1982).

Rossi et al., "Palladium-Catalyzed Syntheses of Naturally-Occurring acetylenic Thiophens and Related Compounds", Tetrahedron, vol. 40, pp. 2773-2779, (1984).

Saito et al., "A Synthesis of Biaryls via Nickel (O)-Catalyzed Cross-Coupling Reaction of Chloroarenes with Phenylboronic Acids", Tetrahedron Letters, vol. 37, pp. 2993-2996, (1996).

Sanisbury, "Modern Methods of Aryl-Aryl Bond Formation", Tetrahedron, vol. 36, pp. 3327 to 3359, (1980).

Silbille et al., "Electrochemical Conversion of Functionalised Aryl Chlorides and Bromides to Arylzinc Species", Chem. Soc. Chem. Comm., pp. 283-284 (1992).

Sonogashira, et al., "Development of Pd-Cu catalyzed cross-coupling of terminal acetylenes with $sp^2$ -carbon halides", Journal of Organo Metallic Chem., vol. 653, pp. 46-49, (2002).

Stanforth, S.P., "Catalytic cross-coupling reactions in Biaryl synthesis," Tetrahedron, vol. 54, pp. 263-303 (1998).

Tamao et al., "Nickel-Phosphine Complex-Catalyzed Grignard Coupling. I. Cross-Coupling of Alkyl, Aryl, and Alkenyl Grignard Reagents with Aryl and Alkenyl Halides: General Scope and Limitations", Bull. Chem. Soc. Japan, vol. 49, pp. 1958-1969, (1976).

Voegtle et al., "Tweezer-shaped hydrocarbons", Chemical Abstracts, vol. 125, pp. 219-235 (1992).

Wenkert, et al., "Transformation of Carbon-Oxygen into Carbon-Carbon Bonds Mediated by Low-Valent Nickel Species", Journal of Organic Chemistry, vol. 49, pp. 4894-4899, (1984).

Wenkert, et al., "Nickel-Induced Conversion of Carbon-Oxygen into Carbon-Carbon Bonds, One-Step Transformations of Enol Ethers into Olefins and Aryl Ethers into Biaryls", vol. 101, pp. 2246-2247, (1979).

Whitall et al, "Organometallic Complexes for Nonlinear Optics. 3.1 Molecular Quadratic Hyperpolarizabilities of Ene-, Imine-, and Azo-Linked Buthenium, sigma, -Acetylides: Z-ray Crystal Structure of Ru (E) -4, 4'-C. tplbond.CC6H4CH: CH6H4NO2: (PPh3) 2 (.eta. -C5H5)", Organometallics, 15(7), pp. 1935-1941, (1996).

Zembayashi et al., "Nickel-Phosphine Complex-Catalyzed Homo Coupling of Aryl Halides in the Presence of Zinc Powder", Tetrahedron Letters No. 47, pp. 4089-4092 (1977).

Zhu et al., "The Direct Formation of Functionalized Alkyl(aryl)zinc Halides by Oxidative Addition of Highly Reactive Zinc with Organic Halides and Their Reactions with Acid Chlorides, alpha beta. -Unsaturated Ketones, and Allylic, Aryl, and Vinyl Halides", J. Org. Chem., vol. 56, pp. 1445-1453 (1991).

* cited by examiner dcument # PROCESS FOR PREPARING ALKYNYL-SUBSTITUTED AROMATIC AND HETEROCYCLIC COMPOUNDS

BACKGROUND OF THE INVENTION

This invention relates to a process for the production of alkynylated aromatic and heterocyclic compounds, and more specifically to such a process in which the alkynylated compound is produced using an aryl or heterocyclic nitrile as a starting reagent.

A variety of methods have been described for preparation of aromatic or heterocyclic alkynyl compounds. Many of them involve a catalytic reaction in which an aromatic, heterocyclic, or other halide is a reagent. Some others proceed through an intermediate propargyl or other alkynyl alcohol. Still others proceed by different routes.

For example, Zimmer et al., U.S. Pat. No. 5,202,349, disclose (column 9) the production of certain pharmaceutically active substituted phenylacetylenes in which the acetylenic group is further substituted by an aromatic or heterocyclic group, by reaction of a type of substituted phenyl bromide or iodide with an aromatic or heterocyclic acetylene, or of a similar type of substituted phenylacetylene with an aromatic or heterocyclic bromide or iodide, in the presence of a tertiary amine, a palladium complex catalyst, and optionally a catalytic amount of cuprous iodide.

Dieck et al., *Organometallic Chem.* 93:259 (1975) disclose production of substituted acetylenes by reaction of aryl and vinylic halides with phenylacetylene and three aliphatic alkynes in the presence of palladium acetate catalyst and an amine. Rossi et al., *Tetrahedron* 40:2773 (1984) disclose production of acetylenes substituted by bithienyl and phenylthienyl groups, by reaction of the corresponding bithienyl or phenylthienyl iodide with trimethylsilylethynyl magnesium bromide, followed by reaction of the thus produced substituted acetylene with, for example, monobromoethylene.

Similarly, in Kirchoff et al., U.S. Pat. No. 4,724,260,1-trimethylsilyl-2-(4-benzocyclobutyl)acetylene was prepared by reaction of trimethylsilylacetylene and 4-bromobenzocyclobutane in the presence of a catalyst, e.g. palladium (II) chloride, triphenylphosphine and cuprous iodide. Aryl alkynes were produced from aryl halides and a terminal alkyne by a generally similar reaction in Zhi et al, U.S. Pat. No. 6,566,372 (col. 67, e.g.). Tegeler et al. U.S. Pat. No. 6,500,849 disclose production of pyridyl aryl alkynes by reaction of a halopyridine with an aryl alkyne (col. 11, e.g.) in the presence of a similar catalyst and an acid acceptor.

Beletskaya et al., *Tetrahedron Letters* 44:5011 (2003) describe the Sonogashira-Hagihara reaction, a coupling of a terminal acetylene with an aryl iodide in the presence of a nickel catalyst. Sonogashira, *J. Organomet. Chem.* 653:46 (2002) further describes palladium-copper cross-coupling of terminal acetylenes with halides.

Chandaratna, U.S. Pat. No. 5,264,456, also disclose reaction between an acetylenic compound and a halide, in this case between either a substituted phenylethyne or a zinc salt of such a compound, and a substituted halide, in the presence of cuprous iodide and a palladium complex.

Brunner et al., U.S. Pat. No. 4,508,560, disclose the production of certain herbicidal heterocyclyl/aryl acetylenic compounds by reaction of a phenyl, naphthyl or heterocyclic acetylene with a substituted heterocyclic halide in which the heterocyclic group contains a 5- or 6-membered ring. The same patent also discloses an alternate process for preparing such compounds, in which the substituted heterocyclic halide is reacted with an aryl- or heterocyclic-substituted propargyl alcohol in the presence of a strong base and a metal catalyst. Another patent by Brunner et al., U.S. Pat. No. 4,412,856, discloses similar processes for the production of certain herbicidal diaryl or aryl/heterocyclyl substituted acetylenes.

Another reaction for producing such compounds, namely that involving an aryl compound having a leaving group such as a sulfonate, is disclosed in Babb et al., U.S. Pat. No. 6,252,001.

Reiffenrath et al., U.S. Pat. No. 5,084,204, discloses several processes for the preparation of disubstituted acetylenes. These include (a): brominating and then dehydrohalogenating the corresponding stilbenes; (b) reacting a compound having a methylene-ketonic group in the position where a triple bond is desired with an inorganic acid chloride, followed by dehydrohalogenation; (c) reacting such a compound with semicarbazide and selenium dioxide, followed by warming in the presence of methyllithium; (d) coupling of an aryl zinc compound with an aryl halide; (e) rearrangement of a 1,1-diaryl-2-halogenoethylene; (f) reacting a 4-substituted phenyl- or cyclohexylacetylene with an aryl halide; and (g) adding a hydrogen halide to a cyclohexene derivative.

Benzonitriles are readily available substrates, yet the development of processes for producing substituted alkynyl aromatic compounds has focused primarily, even nearly entirely, on processes for producing such compounds from aryl halides. A process that enables production of such compounds from benzonitriles and other aryl or heterocyclic nitrites would be welcome.

BRIEF SUMMARY OF THE INVENTION

This invention is a process for the production of mono-or disubstituted aryl (including heterocyclic) acetylenes comprising reacting an aryl nitrile with an alkynylzinc compound, a bis-alkynylzinc compound, or an alkynylmagnesium compound in the presence of a nickel/phosphine catalyst to produce an aryl- or heterocyclic-substituted alkyne.

DETAILED DESCRIPTION OF THE INVENTION

In the process of this invention, an aryl or aromatic nitrile having the formula Ar—CN is reacted with an alkynylzinc or alkynylmagnesium compound having the formula RC≡C—M—X, or with a bis-alkynylzinc compound having the formula RC≡C—Zn—C≡CR, in the presence of a catalyst comprising nickel and a phosphine ligand, to produce a mono- or disubstituted acetylene compound Ar—C≡CR. In this process, Ar represents an optionally substituted aromatic moiety as defined herein, R represents a hydrogen atom, an optionally substituted aromatic moiety, an optionally substituted aliphatic moiety, or a silyl group, all as defined herein; M represents zinc or magnesium; and X represents Cl, Br, I a catecholate group or a group —OR$_1$ or —SR$_1$ in which R$_1$ represents optionally substituted C$_1$–C$_8$ alkyl, optionally substituted aryl, or optionally substituted aryl (C$_1$–C$_8$)alkyl. In the products of the process, one moiety (Ar, that generated by the aryl nitrile) is an optionally substituted aromatic moiety, and the other (R, generated from the zinc or magnesium compound) is hydrogen, an optionally substituted aromatic moiety, an optionally substituted aliphatic moiety, or a silyl group. Preferably Ar is not 2-pyridyl, that is, the aromatic nitrile is not 2-cyanopyridine; up to now we have not been able to produce more than trace amounts of product by this process. However, R may be a 2-pyridyl moiety.

Definitions

As used herein,

"Aromatic" or "aryl" refers to the typical substituted or unsubstituted non-aliphatic hydrocarbyl or heterocyclic groups of this class, i.e., a polyunsaturated, typically aromatic, hydrocarbyl cyclical, or heterocyclic, substituent, which can have a single ring or multiple rings (up to three rings) that are fused together or linked covalently. Typical hydrocarbyl aromatic groups include phenyl, naphthyl, anthracenyl, acenaphthyl, biphenylenyl, fluorenyl, phenanthrenyl, phenalenyl, indanyl, and the like. Also included are aryl groups substituted by other aryl groups, such as biphenyl. Preferred substituents for such hydrocarbyl aromatic groups include halogen, hydroxy, optionally substituted lower alkyl, optionally substituted lower alkoxy, and amino (or combinations of these). Heterocyclic aryl or aromatic groups refers to unsaturated cyclical moieties containing carbon atoms in the ring and additionally one or more hetero atoms, which are typically oxygen, nitrogen, sulfur and/or phosphorus, such as pyridyl, thienyl, furyl, thiazolyl, pyranyl, pyrrolyl, pyrazolyl, imidazolyl, pyrazinyl, thiazolyl, and fused-ring moieties such as benzoxazolyl, benzthiazolyl, etc. Typically, such heterocyclic groups comprise from 5 to 13 ring atoms and from one to three hetero atoms. Such moieties are optionally substituted with one or more substituents such as halogen, hydroxy, optionally substituted lower alkyl, optionally substituted lower alkoxy, amino, amide, ester moieties and carbonyl moieties (i.e., aldehyde or ketonic moieties). Preferred heterocyclic moieties in the processes and compounds of the invention are pyridyl, furyl, thienyl and pyrazolyl.

More generally, substituents in substituted aryl groups Ar can be any substituent that does not interfere with the coupling reaction, including alkyl (preferably $C_1$–$C_{12}$), alkenyl (preferably $C_2$–$C_{12}$), alkynyl (preferably $C_2$–$C_{12}$), alkoxy (preferably $C_1$–$C_{12}$), acyloxy (preferably $C_1$–$C_{12}$), alkyleneoxy (preferably $C_1$–$C_3$), alkylenedioxy (preferably $C_1$–$C_3$), aryloxy, aryl, heteroaryl, F, Cl, OH, $NO_2$, COOH, CHO, $SO_3H$, $SO_2$, SOR, $NH_2$, NH-alkyl (preferably $C_1$–$C_{12}$), N-dialkyl (preferably $C_1$–$C_{12}$), haloalkyl (e.g., trihalomethyl), haloalkoxy (e.g., trifluoromethoxy), NHCO-alkyl (preferably $C_1$–$C_8$), CONH-alkyl (preferably $C_1$–$C_4$), CON-dialkyl (preferably $C_1$–$C_4$), COO-alkyl (preferably $C_1$–$C_{12}$), $CONH_2$, CO-alkyl (preferably $C_1$–$C_{12}$), NHCOH, NHCOO-alkyl (preferably $C_1$–$C_8$), CO-aryl, COO-aryl, $CHCHCO_2$-alkyl (preferably $C_1$–$C_{12}$), $CHCHCO_2H$, PO-diaryl, and PO-dialkyl (preferably $C_1$–$C_8$). One of skill in the art will understand that the presence of a substituent having an active hydrogen atom (e.g., OH, COOH, CONH-alkyl and the like) will consume an equivalent molar amount of the organomagnesium or organozinc reagent, such that an excess of the organometallic reagent will be desired for higher yield coupling reactions.

"Aliphatic" means a straight or branched chain, or non-aromatic cyclical, hydrocarbon radical, or combination thereof, which may be fully saturated, or mono- or polyunsaturated having the number of carbon atoms designated (i.e. $C_1$–$C_{10}$ means one to ten carbon atoms). Examples of saturated acyclic aliphatic groups (also termed alkyl groups) include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated aliphatic group is one having one or more double bonds or triple bonds. Examples of unsaturated acyclic aliphatic groups include optionally substituted alkenyl and alkynyl groups such as vinyl, 2-propenyl, isopropenyl, crotyl, 2-isopentenyl, 2-(butadienyl), 2,4-pentadienyl, 3-(1,4-pentadienyl), 3-propynyl, 3-butynyl, and the higher homologs and isomers. Examples of cyclical aliphatic groups include cyclopropyl, cyclobutyl, cyclopentyl, cyclohexyl, cyclopentenyl, cyclohexenyl, cyclohexadienyl, and the like. Examples of combinations of cyclical and acyclic aliphatic groups include cyclopropylmethyl, cyclohexylmethyl, and the like. The terms "lower alkyl" and "lower alkenyl" mean a group of the type mentioned, having up to six carbon atoms. For use in the invention, aliphatic groups generally may be of any desirable size. Preferably they will contain up to 20, most preferably, up to 10, carbon atoms.

The aliphatic groups used in this invention may be unsubstituted or may be mono- or polysubstituted. Substituents include a variety of groups selected from: —OR', =O, =NR', =N—OR', —NR'R", —SR', =S, -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NRR'R")=NR'", —NR'C(NR'R")=NR'", —NR—C(NR'R")=NR'", —S(O)R', —S(O)$_2$R', —S(O)$_2$NR'R", —NRSO$_2$R', —CN and —$NO_2$, in a number ranging from zero to (2m'+1), where m' is the total number of carbon atoms in such radical. R', R" and R'" each independently may be hydrogen, optionally substituted alkyl, aryl optionally substituted with 1–3 halogens, optionally substituted alkoxy, optionally substituted alkenoxy, optionally substituted thioalkoxy or optionally substituted aryl-($C_1$–$C_4$)alkyl groups. When a compound of the invention includes more than one R group, for example, each of the R groups is independently selected as are each R', R" and R'" groups when more than one of these groups is present. When R' and R" are attached to the same nitrogen atom, they can be combined with the nitrogen atom to form a 5-, 6-, or 7-membered ring, for example, 1-pyrrolidinyl or 4-morpholinyl.

Substituted aliphatic groups also include arylaliphatic groups, namely aliphatic groups substituted by one or more aryl groups; for instance, benzyl, phenethyl, triphenylmethyl, styryl, and the like. The aromatic ring or rings and/or the aliphatic portion of the arylaliphatic groups may be further substituted similarly to other groups, e.g. chlorobenzyl, methylbenzyl, etc. Substituted aliphatic groups also include aliphatic groups substituted by one or more saturated or unsaturated heterocyclic groups, e.g., pyridylmethyl, pyridylethyl, piperidinylmethyl, pyrrolidinylmethyl, morpholinylmethyl, quinolylmethyl, etc. Heterocyclic rings of such groups may be substituted by one or more halogens, hydroxyl groups, lower alkyl groups, or lower alkoxy groups (including combinations of such groups).

"Silyl" refers to silicon atoms, preferably substituted and most preferably trisubstituted, that is, groups having the formula $R_aR_bR_cSi$— in which $R_a$, $R_b$ and $R_c$ are independently hydrogen or optionally substituted aliphatic or aryl moieties. Preferably at least two of $R_a$, $R_b$ and $R_c$ are not hydrogen, and most preferably none of them are hydrogen. Typical substituents on the silicon atom include methyl, ethyl, methoxy, ethoxy and phenyl. A preferred silyl moiety is trimethylsilyl. Substituents may also include halo-substituted aliphatic moieties providing they do not react with the alkynyl zinc or magnesium reagent. For example, chloromethyl substituents on the silicon atom are likely to produce such an undesirable reaction, whereas chloroethyl and chlorinated alkyl groups having three or more carbon atoms are less likely to produce such a reaction.

In one embodiment, the process of this invention comprises reacting an aryl nitrile having the formula Ar—CN, where Ar is an optionally substituted hydrocarbyl or heterocyclic aromatic moiety, with an alkynylzinc or alkynylmagnesium compound having the formula RC≡CM—X, in which M represents zinc or magnesium and X is as defined above, or with a bis-alkynylzinc compound having the formula RC≡C—Zn—C≡CR, in which R also is an optionally substituted hydrocarbyl or heterocyclic aromatic moiety. In such a process, Ar and R may represent the same or different aryl groups. Thus the resulting products Ar—C≡C—R are symmetrical or asymmetrical di-aromatic substituted acetylenes. In asymmetric compounds in which Ar is a heterocyclic aromatic moiety, it is preferably an optionally substituted pyridyl or furyl group, and in such compounds R is preferably an optionally substituted phenyl group.

In another embodiment the aromatic nitrile Ar—CN is reacted with an alkynylzinc or alkynylmagnesium compound having the formula RC≡CM—X, or with a bis-alkynylzinc compound having the formula RC≡C—Zn—C≡CR, in which R is an optionally substituted aliphatic group. The products of this process are disubstituted acetylenes in which one substituent is a group Ar, while the other is an aliphatic moiety.

In a third embodiment the aromatic nitrile Ar—CN is reacted with an alkynylzinc or alkynylmagnesium compound having the formula RC≡CM—X, or with a bis-alkynylzinc compound having the formula RC≡C—Zn—C≡CR, in which R is hydrogen. The products of this embodiment are monosubstituted acetylenes having the formula Ar—C≡CH.

The catalyst for the reaction comprises nickel and a phosphine ligand selected from those having the formula $CH_3P(R_2)(R_3)$ in which $R_2$ and $R_3$ may be the same or different and are selected from $C_1$–$C_{12}$ alkyl (preferably $C_1$–$C_6$ alkyl), $C_1$–$C_{12}$ alkoxy (preferably $C_1$–$C_6$ alkoxy), aryl, and aryloxy (where "aryl" is as defined herein, and is preferably optionally substituted phenyl). Preferred phosphine ligands are trimethylphosphine and bis(dimethylphosphino)-ethane. The catalyst may be added as such, or may be formed in situ, as shown in some of the examples, for instance, from a nickel compound such as nickel acetylacetonate or nickel cyanide and the appropriate phosphine. Generally, either the alkynylzinc reagent or the alkynylmagnesium reagent in the reaction mixture is capable of reducing the nickel(II) to generate the active catalyst in situ, with concomitant generation of the desired substituted acetylene. This can, if necessary, be determined by routine experimentation. Suitable reductants for ex situ generation of the active catalyst from nickel(II) sources are known in the art and include organomagnesium halide reagents (e.g. methylmagnesium halide) and various hydride reagents [e.g. sodium bis(2-methoxyethoxy) aluminum dihydride].

Preformed nickel catalysts, for example, dichlorobis(trimethylphosphine)nickel, generally give slightly better results than catalysts prepared in situ (e.g., nickel acetylacetonate+trimethylphosphine). The preferred phosphine ligand is trimethylphosphine. Suitable and optimal ratios of the ligand to catalyst metal depend on a number of other parameters, including the identity of the ligand, the concentration of the catalyst, the reaction temperature, the reactivity of the reactants, the solvent, and the like, and can be readily determined by routine experimentation. Typically the ratio of the ligand to nickel is in the range of about 1:1 to about 4:1. However, the amount of ligand in the reaction mixture may be in excess of the maximum ratio that could be bound to the catalyst metal. The typical catalyst comprises nickel with two phosphines (i.e., the ratio is about 2:1), for example, dichlorobis(trimethylphosphine)nickel or nickel acetylacetonate+2 eq. trimethylphosphine. The use of excess phosphine, for instance, dichlorobis-(trimethylphosphine)nickel+2 eq. trimethylphosphine or nickel acetylacetonate+4 eq. trimethylphosphine, can accelerate the reaction and give higher yields.

The catalyst loading generally ranges from about 1 to about 25 mol %, based on the aryl nitrile. Catalyst loadings of 5 mol % produce good results with highly reactive substrates; catalyst loadings of 10 mol % are better for less reactive substrates.

The use of various diamine "activators" can increase the rate of the reaction. These activators can be primary, secondary or tertiary diamines. The preferred activators for this process are N,N,N',N'-tetramethylethylenediamine and N,N,N',N'-tetramethyl-1,4-butanediamine.

Among the aromatic nitrile reagents that may be used in this process, electron-deficient or neutral benzonitriles tend to work well. On the other hand, electron-rich aryl nitrites (e.g., 4-dimethylaminobenzonitrile or 4-methoxybenzonitrile) are slower to react. Nitriles with potentially reactive functional groups (e.g., —Cl, —F, —NH₂) nonetheless react cleanly in this process.

Alkynylzinc salts are known in the art and have the general formula RC≡C—M—X wherein M is Zn and R and X are as defined above. The identity of the anion X can be varied but it must not interfere with the reaction. Suitable anions can be determined by routine experimentation. Preferred alkynylzinc compounds are halides. Especially preferred are alkynylzinc chloride and alkynylzinc bromide reagents.

Alkynylzinc reagents RC≡C—Zn—X may be obtained by various methods known in the art, for instance, as shown in the examples, by combining an alkyllithium compound such as methyllithium with the substituted alkyne ArC≡CH, and then with a zinc compound, for example, zinc dibromide. Alternatively, they may be prepared by similar reaction of an alkynyl Grignard reagent with a zinc compound, or reaction of a 1-halo-1-alkyne with zinc metal.

Suitable alkynylmagnesium reagents are known in the art and have the formula RC≡CM—X wherein M is Mg and R and X are as defined above. Such alkynylmagnesium halides are among the class of compounds known as Grignard reagents, and may be prepared by any of the ways known to prepare such reagents. In general, the alkynylmagnesium reagents of this process are prepared by reaction of an alkyl Grignard reagent with a 1-alkyne.

Bis-alkynyl zinc compounds RC≡C—Zn—C≡CR are prepared by combining an alkynylmagnesium reagent RC≡C—Mg—X with a zinc compound in a 2:1 molar ratio, for example zinc dibromide or zinc dichloride, for instance, as shown in example 21. Alternatively, they may be prepared by similar reaction of an alkynyl lithium reagent with zinc chloride or zinc bromide.

Among the alkynyl reactants, alkynylzinc reagents are much more active than alkynylmagnesium reagents; the latter tend to give lower yields of the arylalkyne products as well as large amounts of homocoupled diynes.

Among the reagents for use in this process, the alkynylzinc halides react to give higher yields of the arylalkyne products than do the corresponding bisalkynylzinc reagents Alkynylzinc bromides appear to give slightly higher yields than alkynylzinc chlorides or alkynylzinc catecholates.

Additionally, alkylalkynylzinc bromides (e.g., 1-hexynylzinc bromide) react faster than the corresponding arylalkynylzinc bromides (e.g., phenethynylzinc bromide).

The optimum stoichiometry of alkynylzinc bromide to aryl nitrile is 2:1; ratios of 1:1 or 3:1 tend to give lower yields. The optimum stoichiometry of alkynylzinc chloride to aryl nitrile is 3:1; ratios of 2:1 or 4:1 tend to give lower yields. Alkynylzinc bromides prepared from alkynyllithiums appear to give higher yields than those prepared from alkynylmagnesium bromides In general the process of this invention is carried out at a temperature ranging from about 25 to about 100° C., preferably from about 35 to about 70° C., in an inert solvent system, which preferably comprises an aprotic solvent. The reaction may conveniently be carried out at the refluxing temperature of the solvent. Inert solvents are those that do not react with either the reactants or the products of this process, or with the catalyst. The term "solvent system" is used to indicate that a single solvent or a mixture of two or more solvents may be used. Suitable solvents include tetrahydrofuran (THF), 2-methyltetrahydrofuran, 1,3-dioxane, 1,4-dioxane, dimethylformamide (DMF), 1-methyl-2-pyrrolidinone, diglyme and toluene, and combinations of these. Of these solvents, THF is preferred. In general, the reaction is carried out at about atmospheric pressure, or slightly above.

The reaction components can be combined in essentially any order. For those reactions run at elevated temperatures, the reaction components can be combined prior to heating to the reaction temperature, or one or more components may be added when the other components have been brought to the desired reaction temperature. The preferred order of addition for any specific embodiment can be determined by routine experimentation with a view towards both reaction performance and chemical engineering considerations.

The desired product of the reaction, a mono- or disubstituted alkyne, may be recovered from the reaction mixture by distillation, crystallization, chromatography, or extraction, as appropriate to the product. As known in the art, for example in the patents and literature cited in the Background section above, the products of this process may variously be pharmaceutically or pesticidally active compounds, or intermediates for them, or may be useful as reagents in various processes, as known in the art.

In a commercial operation the reaction may be conducted as a batch or as a continuous process, as most appropriate. Commercial installations for conducting the reaction will have appropriate means for feeding reagents and catalysts, recovering desired products, recovery and disposal or recycling of byproducts or of unreacted starting materials, distillation or other separation of various substances, catalyst recovery or regeneration, and the like.

In any event, the necessary or optimal reaction parameters for carrying out the processes of this invention, including (but not limited to) temperature, time, pressure, ratio of reactants, selection of catalysts, concentration of catalysts, ratio of catalyst to aryl nitrile, nature of substituent groups, use of initiators, and the like, may be readily determined empirically.

The following represent examples of the processes of this invention. A summary of reactants and products is contained in the following Table 1.

EXAMPLE 1

This example illustrates the preparation of diphenylacetylene by a nickel catalyzed coupling of benzonitrile with phenylethynylzinc bromide (Table 1, entry 1).

A solution of phenylacetylene (0.439 ml; 0.409 g; 4.00 mmol) in THF (2 ml) was treated at 0° C. with n-butyllithium (1.6 ml; 4.0 mmol; 2.5 M in hexanes) and the resulting solution was allowed to warm to room temperature for 15 min. The solution was cooled to 0° C., then treated with a solution of $ZnBr_2$ (0.901 g; 4.00 mmol) in THF (2 ml) and allowed to warm to room temperature for 30 min. Solvent was removed in vacuo, then THF (2 ml) was added. This solution was then added to a room temperature solution of benzonitrile (0.204 ml; 0.206 g; 2.00 mmol), dichlorobis(trimethylphosphine)nickel (0.0564 g; 10 mol %), and tridecane (internal GC analytical standard) (0.244 ml; 0.184 g; 1.00 mmol) in THF (2 ml). The reaction mixture was then heated to 65° C. and stirred for 41 h; then a sample was withdrawn and quenched in a mixture of 1 M sodium citrate (aq) and MTBE (methyl t-butyl ether). GC analysis of the organic phase of the hydrolyzed reaction sample showed the presence of 1.58 mmol (79% yield) of diphenylacetylene and 0.20 mmol of benzonitrile remaining in the reaction mixture.

EXAMPLE 2

This example illustrates the use of less dichlorobis(trimethylphosphine)nickel catalyst (5% vs 10% as used in Example 1) to prepare diphenylacetylene by a nickel catalyzed coupling of benzonitrile with phenylethynylzinc bromide.

A solution of phenylacetylene (0.439 ml; 0.409 g; 4.00 mmol) in THF (2 ml) was treated at 0° C. with n-butyllithium (1.6 ml; 4.0 mmol; 2.5 M in hexanes) and the resulting solution was allowed to warm to room temperature for 10 min. The solution was cooled to 0° C., then treated with a solution of $ZnBr_2$ (0.923 g; 4.10 mmol) in THF (2 ml) and allowed to warm to room temperature for 30 min. Solvent was removed in vacuo, then THF (2 ml) was added. This solution was then added to a room temperature solution of benzonitrile (0.204 ml; 0.206 g; 2.00 mmol), dichlorobis(trimethylphosphine)nickel (0.0282 g; 5 mol %), and tridecane (0.244 ml; 0.184 g; 1.00 mmol) in THF (2 ml). The reaction mixture was then heated to 65° C. and stirred for 96 h; then a sample was withdrawn and quenched in a mixture of 1 M sodium citrate (aq) and MTBE. GC analysis of the organic phase of the hydrolyzed reaction sample showed the presence of 1.00 mmol (50% yield) of diphenylacetylene and 0.54 mmol of benzonitrile remaining in the reaction mixture.

EXAMPLE 3

This example illustrates the use of an additional 10% trimethylphosphine with the 5 mol % dichlorobis(trimethylphosphine)nickel used in Example 2 to prepare diphenylacetylene by a nickel catalyzed coupling of benzonitrile with phenylethynylzinc bromide.

A solution of phenylacetylene (0.439 ml; 0.409 g; 4.00 mmol) in THF (2 ml) was treated at 0° C. with n-butyllithium (1.6 ml; 4.0 mmol; 2.5 M in hexanes) and the resulting solution was allowed to warm to room temperature for 10 min. The solution was cooled to 0° C., then treated with a solution of $ZnBr_2$ (0.901 g; 4.00 mmol) in THF (2 ml) and allowed to warm to room temperature for 30 min.

Solvent was removed in vacuo, then THF (2 ml) was added. This solution was then added to a room temperature solution of benzonitrile (0.204 ml; 0.206 g; 2.00 mmol), dichlorobis(trimethylphosphine)nickel (0.0282 g; 5 mol %), trimethylphosphine (0.20 ml; 0.20 mmol; 1.0 M in THF), and tridecane (0.244 ml; 0.184 g; 1.00 mmol) in THF (2 ml). The reaction mixture was then heated to 65° C. and stirred for 44 h; then a sample was withdrawn and quenched in a mixture of 1 M sodium citrate (aq) and MTBE. GC analysis of the organic phase of the hydrolyzed reaction sample showed the presence of 1.43 mmol (72% yield) of diphenylacetylene and 0.36 mmol of benzonitrile remaining in the reaction mixture.

EXAMPLE 4

This example illustrates the use of N,N,N',N'-tetramethylethylenediamine as an activator with the 5 mol % dichlorobis(trimethylphosphine)nickel used in Example 2 to prepare diphenylacetylene by a nickel catalyzed coupling of benzonitrile with phenylethynylzinc bromide.

A solution of phenylacetylene (0.439 ml; 0.409 g; 4.00 mmol) in THF (2 ml) was treated at 0° C. with n-butyllithium (1.6 ml; 4.0 mmol; 2.5 M in hexanes) and the resulting solution was allowed to warm to room temperature for 10 min. The solution was cooled to 0° C., then treated with a solution of $ZnBr_2$ (0.901 g; 4.00 mmol) in THF (2 ml) and allowed to warm to room temperature for 30 min. Solvent was removed in vacuo, then THF (2 ml) was added. This solution was then added to a room temperature solution of benzonitrile (0.204 ml; 0.206 g; 2.00 mmol), dichlorobis(trimethylphosphine)nickel (0.0282 g; 5 mol %), N,N,N',N' tetramethylethylenediamine (0.151 ml; 0.116 g; 1.00 mmol), and tridecane (0.244 ml; 0.184 g; 1.00 mmol) in THF (2 ml). The reaction mixture was then heated to 65° C. and stirred for 67 h; then a sample was withdrawn and quenched in a mixture of 1 M sodium citrate (aq) and MTBE. GC analysis of the organic phase of the hydrolyzed reaction sample showed the presence of 1.40 mmol (70% yield) of diphenylacetylene and 0.49 mmol of benzonitrile remaining in the reaction mixture.

EXAMPLE 5

This example illustrates the use of an alternate activator, N,N,N',N'-tetramethyl-1,4-butanediamine, with the 5 mol % dichlorobis(trimethylphosphine)nickel used in Example 2 to prepare diphenylacetylene by a nickel catalyzed coupling of benzonitrile with phenylethynylzinc bromide.

A solution of phenylacetylene (0.439 ml; 0.409 g; 4.00 mmol) in THF (2 ml) was treated at 0° C. with n-butyllithium (1.6 ml; 4.0 mmol; 2.5 M in hexanes) and the resulting solution was allowed to warm to room temperature for 10 min. The solution was cooled to 0° C., then treated with a solution of $ZnBr_2$ (0.901 g; 4.00 mmol) in THF (2 ml) and allowed to warm to room temperature for 30 min. Solvent was removed in vacuo, then THF (2 ml) was added. This solution was then added to a room temperature solution of benzonitrile (0.204 ml; 0.206 g; 2.00 mmol), dichlorobis(trimethylphosphine)nickel (0.0282 g; 5 mol %), N,N,N',N'-tetramethyl-1,4-butanediamine (0.182 ml; 0.144 g; 1.00 mmol), and tridecane (0.244 ml; 0.184 g; 1.00 mmol) in THF (2 ml). The reaction mixture was then heated to 65° C. and stirred for 67 h; then a sample was withdrawn and quenched in a mixture of 1 M sodium citrate (aq) and MTBE. GC analysis of the organic phase of the hydrolyzed reaction sample showed the presence of 1.45 mmol (73% yield) of diphenylacetylene and 0.31 mmol of benzonitrile remaining in the reaction mixture.

EXAMPLE 6

This example illustrates the use of an in situ prepared nickel catalyst from 5% nickel acetylacetonate and 10% trimethylphosphine to prepare diphenylacetylene by a nickel catalyzed coupling of benzonitrile with phenylethynylzinc bromide.

A solution of phenylacetylene (0.439 ml; 0.409 g; 4.00 mmol) in THF (2 ml) was treated at 0° C. with n-butyllithium (1.6 ml; 4.0 mmol; 2.5 M in hexanes) and the resulting solution was allowed to warm to room temperature for 10 min. The solution was cooled to 0° C., then treated with a solution of $ZnBr_2$ (0.901 g; 4.00 mmol) in THF (2 ml) and allowed to warm to room temperature for 30 min. Solvent was removed in vacuo, then THF (2 ml) was added. This solution was then added to a room temperature solution of benzonitrile (0.204 ml; 0.206 g; 2.00 mmol), nickel acetylacetonate (0.0256 g; 5 mol %), trimethylphosphine (0.20 ml; 0.20 mmol; 1.0 M in THF), and tridecane (0.244 ml; 0.184 g; 1.00 mmol) in THF (2 ml). The reaction mixture was then heated to 65° C. and stirred for 73 h; then a sample was withdrawn and quenched in a mixture of 1 M sodium citrate (aq) and MTBE. GC analysis of the organic phase of the hydrolyzed reaction sample showed the presence of 0.84 mmol (42% yield) of diphenylacetylene and 0.51 mmol of benzonitrile remaining in the reaction mixture.

EXAMPLE 7

This example illustrates the use of an in situ prepared nickel catalyst from 5% nickel acetylacetonate and 20% trimethylphosphine to prepare diphenylacetylene by a nickel catalyzed coupling of benzonitrile with phenylethynylzinc bromide.

A solution of phenylacetylene (0.439 ml; 0.409 g; 4.00 mmol) in THF (2 ml) was treated at 0° C. with n-butyllithium (1.6 ml; 4.0 mmol; 2.5 M in hexanes) and the resulting solution was allowed to warm to room temperature for 10 min. The solution was cooled to 0° C., then treated with a solution of $ZnBr_2$ (0.901 g; 4.00 mmol) in THF (2 ml) and allowed to warm to room temperature for 30 min. Solvent was removed in vacuo, then THF (2 ml) was added. This solution was then added to a room temperature solution of benzonitrile (0.204 ml; 0.206 g; 2.00 mmol), nickel acetylacetonate (0.0256 g; 5 mol %), trimethylphosphine (0.40 ml; 0.40 mmol; 1.0 M in THF), and tridecane (0.244 ml; 0.184 g; 1.00 mmol) in THF (2 ml). The reaction mixture was then heated to 65° C. and stirred for 73 h; then a sample was withdrawn and quenched in a mixture of 1 M sodium citrate (aq) and MTBE. GC analysis of the organic phase of the hydrolyzed reaction sample showed the presence of 1.25 mmol (62% yield) of diphenylacetylene and 0.19 mmol of benzonitrile remaining in the reaction mixture.

EXAMPLE 8

This example illustrates the use of an in situ prepared nickel catalyst from an alternate nickel source, 5% nickel cyanide and 10% trimethylphosphine, to prepare diphenylacetylene by a nickel catalyzed coupling of benzonitrile with phenylethynylzinc bromide.

A solution of phenylacetylene (0.439 ml; 0.409 g; 4.00 mmol) in THF (2 ml) was treated at 0° C. with n-butyllithium (1.6 ml; 4.0 mmol; 2.5 M in hexanes) and the resulting solution was allowed to warm to room temperature for 10 min. The solution was cooled to 0° C., then treated with a solution of ZnBr$_2$ (0.901 g; 4.00 mmol) in THF (2 ml) and allowed to warm to room temperature for 30 min. Solvent was removed in vacuo, then THF (2 ml) was added. This solution was then added to a room temperature solution of benzonitrile (0.204 ml; 0.206 g; 2.00 mmol), nickel cyanide tetrahydrate (0.018 g; 5 mol %), trimethylphosphine (0.20 ml; 0.20 mmol; 1.0 M in THF), and tridecane (0.244 ml; 0.184 g; 1.00 mmol) in THF (2 ml). The reaction mixture was then heated to 65° C. and stirred for 73 h; then a sample was withdrawn and quenched in a mixture of 1 M sodium citrate (aq) and MTBE. GC analysis of the organic phase of the hydrolyzed reaction sample showed the presence of 0.80 mmol (40% yield) of diphenylacetylene and 0.56 mmol of benzonitrile remaining in the reaction mixture.

EXAMPLE 9

This example illustrates the use of a different phosphine ligand, bis(dimethylphosphino)ethane, for an in situ prepared nickel catalyst from nickel acetylacetonate to prepare diphenylacetylene by a nickel catalyzed coupling of benzonitrile with phenylethynylzinc bromide.

A solution of phenylacetylene (0.439 ml; 0.409 g; 4.00 mmol) in THF (2 ml) was treated at 0° C. with n-butyllithium (1.6 ml; 4.0 mmol; 2.5 M in hexanes) and the resulting solution was allowed to warm to room temperature for 10 min. The solution was cooled to 0° C., then treated with a solution of ZnBr$_2$ (0.901 g; 4.00 mmol) in THF (2 ml) and allowed to warm to room temperature for 30 min. Solvent was removed in vacuo, then THF (2 ml) was added. This solution was then added to a room temperature solution of benzonitrile (0.204 ml; 0.206 g; 2.00 mmol), nickel acetylacetonate (0.0256 g; 5 mol %), bis(dimethylphosphino)ethane (0.033 ml; 0.030 g; 0.20 mmol), and tridecane (0.244 ml; 0.184 g; 1.00 mmol) in THF (2 ml). The reaction mixture was then heated to 65° C. and stirred for 67 h; then a sample was withdrawn and quenched in a mixture of 1 M sodium citrate (aq) and MTBE. GC analysis of the organic phase of the hydrolyzed reaction sample showed the presence of 0.26 mmol (13% yield) of diphenylacetylene and 1.48 mmol of benzonitrile remaining in the reaction mixture.

EXAMPLE 10

This example illustrates the use of 1,4-dioxane instead of THF as a solvent of Example 1 to prepare diphenylacetylene by a nickel catalyzed coupling of benzonitrile with phenylethynylzinc bromide.

A solution of phenylacetylene (0.439 ml; 0.409 g; 4.00 mmol) in THF (2 ml) was treated at 0° C. with n-butyllithium (1.6 ml; 4.0 mmol; 2.5 M in hexanes) and the resulting solution was allowed to warm to room temperature for 10 min. The solution was cooled to 0° C., then treated with a solution of ZnBr$_2$ (0.923 g; 4.10 mmol) in THF (2 ml) and allowed to warm to room temperature for 30 min. Solvent was removed in vacuo, then 1,4-dioxane (2 ml) was added. This solution was then added to a room temperature solution of benzonitrile (0.204 ml; 0.206 g; 2.00 mmol), dichlorobis(trimethylphosphine)nickel (0.0564 g; 10 mol %), and tridecane (0.244 ml; 0.184 g; 1.00 mmol) in 1,4-dioxane (2 ml). The reaction mixture was then heated to 65° C. and stirred for 42 h; then a sample was withdrawn and quenched in a mixture of 1 M sodium citrate (aq) and MTBE. GC analysis of the organic phase of the hydrolyzed reaction sample showed the presence of 0.88 mmol (44% yield) of diphenylacetylene and 0.51 mmol of benzonitrile remaining in the reaction mixture.

EXAMPLE 11

This example illustrates the use of 1,3-dioxane instead of THF as a solvent of Example 1 to prepare diphenylacetylene by a nickel catalyzed coupling of benzonitrile with phenylethynylzinc bromide.

A solution of phenylacetylene (0.439 ml; 0.409 g; 4.00 mmol) in THF (2 ml) was treated at 0° C. with n-butyllithium (1.6 ml; 4.0 mmol; 2.5 M in hexanes) and the resulting solution was allowed to warm to room temperature for 10 min. The solution was cooled to 0° C., then treated with a solution of ZnBr$_2$ (0.923 g; 4.10 mmol) in THF (2 ml) and allowed to warm to room temperature for 30 min. Solvent was removed in vacuo, then 1,3-dioxane (2 ml) was added. This solution was then added to a room temperature solution of benzonitrile (0.204 ml; 0.206 g; 2.00 mmol), dichlorobis(trimethylphosphine)nickel (0.0564 g; 10 mol %), and tridecane (0.244 ml; 0.184 g; 1.00 mmol) in 1,3-dioxane (2 ml). The reaction mixture was then heated to 65° CX and stirred for 67 h; then a sample was withdrawn and quenched in a mixture of 1 M sodium citrate (aq) and MTBE. GC analysis of the organic phase of the hydrolyzed reaction sample showed the presence of 0.77 mmol (38% yield) of diphenylacetylene and 0.48 mmol of benzonitrile remaining in the reaction mixture.

EXAMPLE 12

This example illustrates the use of 1-methyl-2-pyrrolidinone instead of THF as a solvent of Example 1 to prepare diphenylacetylene by a nickel catalyzed coupling of benzonitrile with phenylethynylzinc bromide.

A solution of phenylacetylene (0.439 ml; 0.409 g; 4.00 mmol) in THF (2 ml) was treated at 0° C. with n-butyllithium (1.6 ml; 4.0 mmol; 2.5 M in hexanes) and the resulting solution was allowed to warm to room temperature for 10 min. The solution was cooled to 0° C., then treated with a solution of ZnBr$_2$ (0.923 g; 4.10 mmol) in THF (2 ml) and allowed to warm to room temperature for 30 min. Solvent was removed in vacuo, then 1-methyl-2-pyrrolidinone (2 ml) was added. This solution was then added to a room temperature solution of benzonitrile (0.204 ml; 0.206 g; 2.00 mmol), dichlorobis(trimethylphosphine)nickel (0.0564 g; 10 mol %), and tridecane (0.244 ml; 0.184 g; 1.00 mmol) in 1-methyl-2-pyrrolidinone (2 ml). The reaction mixture was then heated to 65° C. and stirred for 67 h; then a sample was withdrawn and quenched in a mixture of 1 M sodium citrate (aq) and MTBE. GC analysis of the organic phase of the hydrolyzed reaction sample showed the presence of 0.74 mmol (37% yield) of diphenylacetylene and 0.97 mmol of benzonitrile remaining in the reaction mixture.

EXAMPLE 13

This example illustrates the use of 2-methyltetrahydrofuran instead of THF as a solvent of Example 1 to prepare diphenylacetylene by a nickel catalyzed coupling of benzonitrile with phenylethynylzinc bromide.

A solution of phenylacetylene (0.439 ml; 0.409 g; 4.00 mmol) in THF (2 ml) was treated at 0° C. with n-butyllithium (1.6 ml; 4.0 mmol; 2.5 M in hexanes) and the resulting solution was allowed to warm to room temperature for 10 min. The solution was cooled to 0° C., then treated with a solution of ZnBr$_2$ (0.901 g; 4.00 mmol) in THF (2 ml)

and allowed to warm to room temperature for 30 min. Solvent was removed in vacuo, then 2-methyltetrahydrofuran (2 ml) was added. This solution was then added to a room temperature solution of benzonitrile (0.204 ml; 0.206 g; 2.00 mmol), dichlorobis(trimethylphosphine)nickel (0.0564 g; 10 mol %), and tridecane (0.244 ml; 0.184 g; 1.00 mmol) in 2-methyltetrahydrofuran (2 ml). The reaction mixture was then heated to 65° C. and stirred for 5 days; then a sample was withdrawn and quenched in a mixture of 1 M sodium citrate (aq) and MTBE. GC analysis of the organic phase of the hydrolyzed reaction sample showed the presence of 1.12 mmol (56% yield) of diphenylacetylene and 0.10 mmol of benzonitrile remaining in the reaction mixture.

EXAMPLE 14

This example illustrates the use of toluene instead of THF as a solvent of Example 1 to prepare diphenylacetylene by a nickel catalyzed coupling of benzonitrile with phenylethynylzinc bromide.

A solution of phenylacetylene (0.439 ml; 0.409 g; 4.00 mmol) in THF (2 ml) was treated at 0° C. with n-butyllithium (1.6 ml; 4.0 mmol; 2.5 M in hexanes) and the resulting solution was allowed to warm to room temperature for 10 min. The solution was cooled to 0° C., then treated with a solution of $ZnBr_2$ (0.901 g; 4.00 mmol) in THF (2 ml) and allowed to warm to room temperature for 30 min. Solvent was removed in vacuo, then toluene (2 ml) was added. This solution was then added to a room temperature solution of benzonitrile (0.204 ml; 0.206 g; 2.00 mmol), dichlorobis(trimethylphosphine)nickel (0.0564 g; 10 mol %), and tridecane (0.244 ml; 0.184 g; 1.00 mmol) in toluene (2 ml). The reaction mixture was then heated to 65° C. and stirred for 5 days; then a sample was withdrawn and quenched in a mixture of 1 M sodium citrate (aq) and MTBE. GC analysis of the organic phase of the hydrolyzed reaction sample showed the presence of 0.46 mmol (23% yield) of diphenylacetylene and 0.43 mmol of benzonitrile remaining in the reaction mixture.

EXAMPLE 15

This example illustrates the use of one equivalent of alkynylzinc bromide instead of the two equivalents used in Example 1 to prepare diphenylacetylene by a nickel catalyzed coupling of benzonitrile with phenylethynylzinc bromide.

A solution of phenylacetylene (0.220 ml; 0.204 g; 2.00 mmol) in THF (2 ml) was treated at 0° C. with n-butyllithium (0.8 ml; 2.0 mmol; 2.5 M in hexanes) and the resulting solution was allowed to warm to room temperature for 15 min. The solution was cooled to 0° C., then treated with a solution of $ZnBr_2$ (0.450 g; 2.00 mmol) in THF (1 ml) and allowed to warm to room temperature for 30 min. Solvent was removed in vacuo, then THF (2 ml) was added. This solution was then added to a room temperature solution of benzonitrile (0.204 ml; 0.206 g; 2.00 mmol), dichlorobis(trimethylphosphine)nickel (0.0564 g; 10 mol %), and tridecane (0.244 ml; 0.184 g; 1.00 mmol) in THF (3 ml). The reaction mixture was then heated to 65° C. and stirred for 65 h; then a sample was withdrawn and quenched in a mixture of 1 M sodium citrate (aq) and MTBE. GC analysis of the organic phase of the hydrolyzed reaction sample showed the presence of 0.66 mmol (33% yield) of diphenylacetylene and 1.26 mmol of benzonitrile remaining in the reaction mixture.

EXAMPLE 16

This example illustrates the use of three equivalents of alkynylzinc bromide instead of the two equivalents used in Example 1 to prepare diphenylacetylene by a nickel catalyzed coupling of benzonitrile with phenylethynylzinc bromide.

A solution of phenylacetylene (0.659 ml; 0.613 g; 6.00 mmol) in THF (2 ml) was treated at 0° C. with n-butyllithium (2.4 ml; 6.0 mmol; 2.5 M in hexanes) and the resulting solution was allowed to warm to room temperature for 15 min. The solution was cooled to 0° C., then treated with a solution of $ZnBr_2$ (1.35 g; 6.00 mmol) in THF (3 ml) and allowed to warm to room temperature for 30 min. Solvent was removed in vacuo, then THF (2 ml) was added. This solution was then added to a room temperature solution of benzonitrile (0.204 ml; 0.206 g; 2.00 mmol), dichlorobis(trimethylphosphine)nickel (0.0564 g; 10 mol %), and tridecane (0.244 ml; 0.184 g; 1.00 mmol) in THF (1 ml). The reaction mixture was then heated to 65° C. and stirred for 65 h; then a sample was withdrawn and quenched in a mixture of 1 M sodium citrate (aq) and MTBE. GC analysis of the organic phase of the hydrolyzed reaction sample showed the presence of 1.30 mmol (65% yield) of diphenylacetylene and 0.20 mmol of benzonitrile remaining in the reaction mixture.

EXAMPLE 17

This example illustrates the use of an alkynylzinc chloride reagent instead of the alkynylzinc bromide reagent of Example 1 to prepare diphenylacetylene by a nickel catalyzed coupling of benzonitrile with phenylethynylzinc bromide.

A solution of phenylacetylene (0.439 ml; 0.409 g; 4.00 mmol) in THF (2 ml) was treated at 0° C. with n-butyllithium (1.6 ml; 4.0 mmol; 2.5 M in hexanes) and the resulting solution was allowed to warm to room temperature for 15 min. The solution was cooled to 0° C., then treated with a solution of $ZnCl_2$ (0.545 g; 4.00 mmol) in THF (2 ml) and allowed to warm to room temperature for 30 min. Solvent was removed in vacuo, then THF (2 ml) was added. This solution was then added to a room temperature solution of benzonitrile (0.204 ml; 0.206 g; 2.00 mmol), dichlorobis(trimethylphosphine)nickel (0.0564 g; 10 mol %), and tridecane (0.244 ml; 0.184 g; 1.00 mmol) in THF (2 ml). The reaction mixture was then heated to 65° C. and stirred for 43 h; then a sample was withdrawn and quenched in a mixture of 1 M sodium citrate (aq) and MTBE. GC analysis of the organic phase of the hydrolyzed reaction sample showed the presence of 1.16 mmol (58% yield) of diphenylacetylene and 0.66 mmol of benzonitrile remaining in the reaction mixture.

EXAMPLE 18

This example illustrates the use of an alkynyl Grignard reagent (e.g., RMgX; X=halide) instead of the alkynylzinc bromide reagent of Example 2 to prepare diphenylacetylene by a nickel catalyzed coupling of benzonitrile with phenylethynylmagnesium bromide.

A solution of phenylacetylene (0.439 ml; 0.409 g; 4.00 mmol) in THF (4 ml) was treated at 0° C. with ethylmagnesium bromide (4.0 ml; 4.0 mmol; 1.0 M in THF) and the resulting solution was allowed to warm to room temperature for 1 h. This solution was then added to a room temperature solution of benzonitrile (0.204 ml; 0.206 g; 2.00 mmol), dichlorobis(trimethylphosphine)nickel (0.0282 g; 5 mol %), and tridecane (0.244 ml; 0.184 g; 1.00 mmol) in THF (2 ml). The reaction mixture was then heated to 65° C. and stirred for 17 h; then a sample was withdrawn and quenched in a mixture of 1 M sodium citrate (aq) and MTBE. GC analysis of the organic phase of the hydrolyzed reaction sample showed the presence of 0.08 mmol (4% yield) of diphenylacetylene, 0.05 mmol of diphenylbutadiyne, and no benzonitrile remaining in the reaction mixture.

EXAMPLE 19

This example illustrates the use of a bisalkynylzinc reagent instead of the alkynylzinc bromide reagent of Example 2 to prepare diphenylacetylene by a nickel catalyzed coupling of benzonitrile with phenylethynylzinc bromide.

A solution of phenylethynylmagnesium bromide (4.0 ml; 4.00 mmol; 1.0 M in THF) in was treated at room temperature with a solution of $ZnBr_2$ (0.473 g; 2.10 mmol) in THF (1 ml) and stirred for 30 min. This solution was then added to a room temperature solution of benzonitrile (0.204 ml; 0.206 g; 2.00 mmol), dichlorobis(trimethylphosphine)nickel (0.0282 g; 5 mol %), and tridecane (0.244 ml; 0.184 g; 1.00 mmol) in THF (1 ml). The reaction mixture was then heated to 65° C. and stirred for 46 h; then a sample was withdrawn and quenched in a mixture of 1 M sodium citrate (aq) and MTBE. GC analysis of the organic phase of the hydrolyzed reaction sample showed the presence of 0.63 mmol (31% yield) of diphenylacetylene and 0.36 mmol of benzonitrile remaining in the reaction mixture.

EXAMPLE 20

This example illustrates the use of an alkynylzinc catecholate reagent instead of the alkynylzinc bromide reagent of Example 2 to prepare diphenylacetylene by a nickel catalyzed coupling of benzonitrile with phenylethynylzinc bromide.

A solution of catechol (0.440 g; 4.00 mmol) in THF (2 ml) was treated at 0° C. with diethylzinc (4 ml; 4.00 mmol; 1.0 M in THF) and the resulting solution was allowed to warm to room temperature for 20 min. Solvent was removed in vacuo, then phenylethynyllithium (4.0 ml; 4.00 mmol; 1.0 M THF) was added at room temperature and the resulting mixture was stirred for 30 min. This solution was then added to a room temperature mixture of benzonitrile (0.204 ml; 0.206 g; 2.00 mmol), dichlorobis(trimethylphosphine)nickel (0.0282 g; 5 mol %), and tridecane (0.244 ml; 0.184 g; 1.00 mmol). The reaction mixture was then heated to 65° C. and stirred for 6 days; then a sample was withdrawn and quenched in a mixture of 1 M sodium citrate (aq) and MTBE. GC analysis of the organic phase of the hydrolyzed reaction sample showed the presence of 1.08 mmol (54% yield) of diphenylacetylene and 0.41 mmol of benzonitrile remaining in the reaction mixture.

EXAMPLE 21

This example illustrates the preparation of 1-chloro-4-(phenylethynyl)benzene by a nickel catalyzed coupling of 4-chlorobenzonitrile with phenethynylzinc bromide (Table 1, entry 2).

The procedure was identical to Example 1, with the exception that 4-chlorobenzonitrile (0.275 g; 2.00 mmol) was used as a substrate instead of benzonitrile. GC analysis of the organic phase of the hydrolyzed reaction sample after 18 h at 65° C. showed the presence of 1.10 mmol (55% yield) of 1-chloro-4-(phenylethynyl)benzene, 0.09 mmol 1,4-bis(1-phenylethynyl)benzene, and 0.24 mmol of 4-chlorobenzonitrile remaining in the reaction mixture.

EXAMPLE 22

This example illustrates the preparation of 1-methoxy-3-(phenylethynyl)benzene by a nickel catalyzed coupling of 3-methoxybenzonitrile with phenethynylzinc bromide (Table 1, entry 3).

The procedure was identical to Example 1, with the exception that 3-methoxybenzonitrile (0.245 ml; 0.266 g; 2.00 mmol) was used as a substrate instead of benzonitrile. GC analysis of the organic phase of the hydrolyzed reaction sample after 40 h at 65° C. showed the presence of 1.26 mmol (63% yield) of 1-methoxy-3-(phenylethynyl)benzene and 0.43 mmol of 3-methoxybenzonitrile remaining in the reaction mixture.

EXAMPLE 23

This example illustrates the preparation of 2-(phenylethynyl)furan by a nickel catalyzed coupling of 2-furonitrile with phenethynylzinc bromide (Table 1, entry 4).

The procedure was identical to Example 1, with the exception that 2-furonitrile (0.175 ml; 0.186 g; 2.00 mmol) was used as a substrate instead of benzonitrile. GC analysis of the organic phase of the hydrolyzed reaction sample after 18 h at 65° C. showed the presence of 1.26 mmol (74% yield) of 2-(phenylethynyl)furan and no remaining 2-furonitrile in the reaction mixture.

EXAMPLE 24

This example illustrates the preparation of 4-(phenylethynyl)pyridine by a nickel catalyzed coupling of 4-cyanopyridine with phenethynylzinc bromide using 5% catalyst loading (Table 1, entry 5).

The procedure was identical to Example 2, with the exception that 4-cyanopyridine (0.208 g; 2.00 mmol) was used as a substrate instead of benzonitrile. GC analysis of the organic phase of the hydrolyzed reaction sample after 20 h at 65° C. showed the presence of 0.88 mmol (44% yield) of 4-(phenylethynyl)pyridine, and no remaining 4-cyanopyridine in the reaction mixture.

EXAMPLE 25

This example illustrates the preparation of 3-(phenylethynyl)pyridine by a nickel catalyzed coupling of 3-cyanopyridine with phenethynylzinc bromide using 5% catalyst loading (Table 1, entry 6).

The procedure was identical to Example 2, with the exception that 3-cyanopyridine (0.208 g; 2.00 mmol) was used as a substrate instead of benzonitrile. GC analysis of the organic phase of the hydrolyzed reaction sample after 20 h at 65° C. showed the presence of 0.89 mmol (45% yield) of 3-(phenylethynyl)pyridine and no remaining 3-cyanopyridine in the reaction mixture.

EXAMPLE 26

This example illustrates the preparation of 4-(phenylethynyl)-1,1'-biphenyl by a nickel catalyzed coupling of 4-biphenylcarbonitrile with phenethynylzinc bromide (Table 1, entry 7).

The procedure was identical to Example 1, with the exception that 4-biphenylcarbonitrile (0.358 g; 2.00 mmol) was used as a substrate instead of benzonitrile. GC analysis of the organic phase of the hydrolyzed reaction sample after 40 h at 65° C. showed the presence of 1.80 mmol (90% yield) of 4-(phenylethynyl)-1,1'-biphenyl and no remaining 4-biphenylcarbonitrile in the reaction mixture.

EXAMPLE 27

This example illustrates the preparation of 1-octynylbenzene by a nickel catalyzed coupling of benzonitrile with 1-octynylzinc bromide (Table 1, entry 8).

The procedure was identical to Example 1, with the exception that 1-octyne (0.590 ml; 0.441 g; 4.00 mmol) was used as a substrate instead of phenylacetylene. GC analysis of the organic phase of the hydrolyzed reaction sample after 18 h at 65° C. showed the presence of 1.59 mmol (80% yield) of 1-octynylbenzene, and 0.03 mmol of benzonitrile remaining in the reaction mixture.

EXAMPLE 28

This example illustrates the preparation of 1-chloro-4-(1-octynyl)benzene by a nickel catalyzed coupling of 4-chlorobenzonitrile with 1-octynylzinc bromide (Table 1, entry 9).

The procedure was identical to Example 1, with the exception that 1-octyne (0.590 ml; 0.441 g; 4.00 mmol) was used as a substrate instead of phenylacetylene and 4-chlorobenzonitrile (0.275 g; 2.00 mmol) was used as a substrate instead of benzonitrile. GC analysis of the organic phase of the hydrolyzed reaction sample after 23 h at 65° C. showed the presence of 1.41 mmol (70% yield) of 1-chloro-4-(1-octynyl)benzene, 0.11 mmol 1,4-bis(1-octynyl)benzene and no remaining 4-chlorobenzonitrile in the reaction mixture.

EXAMPLE 29

This example illustrates the preparation of 1-methyl-4-(1-octynyl)benzene by a nickel catalyzed coupling of p-tolunitrile with 1-octynylzinc bromide (Table 1, entry 10).

The procedure was identical to Example 1, with the exception that 1-octyne (0.590 ml; 0.441 g; 4.00 mmol) was used as a substrate instead of phenylacetylene and p-tolunitrile (0.239 ml; 0.236 g; 2.00 mmol) was used as a substrate instead of benzonitrile. GC analysis of the organic phase of the hydrolyzed reaction sample after 46 h at 65° C. showed the presence of 1.67 mmol (83% yield) of 1-methyl-4-(1-octynyl)benzene and 0.11 mmol of p-tolunitrile remaining in the reaction mixture.

EXAMPLE 30

This example illustrates the preparation of 2-(1-octynyl)furan by a nickel catalyzed coupling of 2-furonitrile with 1-octynylzinc bromide using 5% catalyst loading (Table 1, entry 11).

The procedure was identical to Example 2, with the exception that 1-octyne (0.590 ml; 0.441 g; 4.00 mmol) was used as a substrate instead of phenylacetylene and 2-furonitrile (0.175 ml; 0.186 g; 2.00 mmol) was used as a substrate instead of benzonitrile. GC analysis of the organic phase of the hydrolyzed reaction sample after 22 h at 65° C. showed the presence of 1.24 mmol (62% yield) of 2-(1-octynyl)furan and no remaining 2-furonitrile in the reaction mixture.

EXAMPLE 31

This example illustrates the preparation of 1-methoxy-3-(1-octynyl)benzene by a nickel catalyzed coupling of 3-methoxybenzonitrile with 1-octynylzinc bromide (Table 1, entry 12).

The procedure was identical to Example 1, with the exception that 1-octyne (0.590 ml; 0.441 g; 4.00 mmol) was used as a substrate instead of phenylacetylene and 3-methoxybenzonitrile (0.245 ml; 0.266 g; 2.00 mmol) was used as a substrate instead of benzonitrile. GC analysis of the organic phase of the hydrolyzed reaction sample after 23 h at 65° C. showed the presence of 1.60 mmol (80% yield) of 1-methoxy-3-(1-octynyl)benzene and no remaining 3-methoxybenzonitrile in the reaction mixture.

EXAMPLE 32

This example illustrates the preparation of 4-(1-octynyl)pyridine by a nickel catalyzed coupling of 4-cyanopyridine with 1-octynylzinc bromide at room temperature using 5% catalyst loading (Table 1, entry 13).

The procedure was identical to Example 2, with the exception that 1-octyne (0.590 ml; 0.441 g; 4.00 mmol) was used as a substrate instead of phenylacetylene and 4-cyanopyridine (0.208 g; 2.00 mmol) was used as a substrate instead of benzonitrile. GC analysis of the organic phase of the hydrolyzed reaction sample after 21 h at room temperature showed the presence of 1.60 mmol (80% yield) of 4-(1-octynyl)pyridine and no remaining 4-cyanopyridine in the reaction mixture.

EXAMPLE 33

This example illustrates the preparation of 1-fluoro-4-(1-octynyl)benzene by a nickel catalyzed coupling of 4-fluorobenzonitrile with 1-octynylzinc bromide using 5% catalyst loading (Table 1, entry 14).

The procedure was identical to Example 2, with the exception that 1-octyne (0.590 ml; 0.441 g; 4.00 mmol) was used as a substrate instead of phenylacetylene and 4-fluorobenzonitrile (0.242 g; 2.00 mmol) was used as a substrate instead of benzonitrile. GC analysis of the organic phase of the hydrolyzed reaction sample after 45 h at 65° C. showed the presence of 1.34 mmol (67% yield) of 1-fluoro-4-(1-octynyl)benzene and no remaining 4-fluorobenzonitrile in the reaction mixture.

EXAMPLE 34

This example illustrates the preparation of 2-(1-octynyl)naphthalene by a nickel catalyzed coupling of 2-naphthonitrile with 1-octynylzinc bromide using 5% catalyst loading (Table 1, entry 15).

The procedure was identical to Example 2, with the exception that 1-octyne (0.590 ml; 0.441 g; 4.00 mmol) was used as a substrate instead of phenylacetylene and 2-naphthonitrile (0.306 g; 2.00 mmol) was used as a substrate instead of benzonitrile. GC analysis of the organic phase of the hydrolyzed reaction sample after 22 h at 65° C. showed the presence of 1.98 mmol (99% yield) of 2-(1-octynyl)naphthalene and no remaining 2-naphthonitrile in the reaction mixture.

EXAMPLE 35

This example illustrates the preparation of 1-hexynylbenzene by a nickel catalyzed coupling of benzonitrile with 1-hexynylzinc bromide (Table 1, entry 16).

The procedure was identical to Example 1, with the exception that 1-hexyne (0.450 ml; 0.329 g; 4.00 mmol) was used as a substrate instead of phenylacetylene. GC analysis of the organic phase of the hydrolyzed reaction sample after 20 h at 65° C. showed the presence of 1.90 mmol (95% yield) of 1-hexynylbenzene and and 0.08 mmol of benzonitrile remaining in the reaction mixture.

EXAMPLE 36

This example illustrates the preparation of 1-chloro-4-(1-hexynyl)benzene by a nickel catalyzed coupling of 4-chlorobenzonitrile with 1-hexynylzinc bromide using 5% catalyst loading (Table 1, entry 17).

The procedure was identical to Example 2, with the exception that 1-hexyne (0.450 ml; 0.329 g; 4.00 mmol) was used as a substrate instead of phenylacetylene and 4-chlorobenzonitrile (0.275 g; 2.00 mmol) was used as a substrate instead of benzonitrile. GC analysis of the organic phase of the hydrolyzed reaction sample after 20 h at 65° C. showed the presence of 1.29 mmol (65% yield) of 1-chloro-4-(1-hexynyl)benzene, 0.10 mmol 1,4-bis(1-hexynyl)benzene and no remaining 4-chlorobenzonitrile in the reaction mixture.

EXAMPLE 37

This example illustrates the preparation of 2-(1-hexynyl)furan by a nickel catalyzed coupling of 2-furonitrile with 1-hexynylzinc bromide (Table 1, entry 18).

The procedure was identical to Example 1, with the exception that 1-hexyne (0.450 ml; 0.329 g; 4.00 mmol) was used as a substrate instead of phenylacetylene and 2-furonitrile (0.175 ml; 0.186 g; 2.00 mmol) was used as a substrate instead of benzonitrile. GC analysis of the organic phase of the hydrolyzed reaction sample after 4 h at 65° C. showed the presence of 1.38 mmol (69% yield) of 2-(1-hexynyl)furan and no remaining 2-furonitrile in the reaction mixture.

EXAMPLE 38

This example illustrates the preparation of 1-(1-hexynyl)-3-methoxybenzene by a nickel catalyzed coupling of 3-methoxybenzonitrile with 1-hexynylzinc bromide (Table 1, entry 19).

The procedure was identical to Example 1, with the exception that 1-hexyne (0.450 ml; 0.329 g; 4.00 mmol) was used as a substrate instead of phenylacetylene and 3-methoxybenzonitrile (0.245 ml; 0.266 g; 2.00 mmol) was used as a substrate instead of benzonitrile. GC analysis of the organic phase of the hydrolyzed reaction sample after 20 h at 65° C. showed the presence of 1.48 mmol (74% yield) of 1-(1-hexynyl)-3-methoxybenzene and no remaining 3-methoxybenzonitrile in the reaction mixture.

EXAMPLE 39

This example illustrates the preparation of 4-(1-hexynyl)-1,1'-biphenyl by a nickel catalyzed coupling of 4-biphenylcarbonitrile with 1-hexynylzinc bromide (Table 1, entry 20).

The procedure was identical to Example 1, with the exception that l-hexyne (0.450 ml; 0.329 g; 4.00 mmol) was used as a substrate instead of phenylacetylene and 4-biphenylcarbonitrile (0.358 g; 2.00 mmol) was used as a substrate instead of benzonitrile. GC analysis of the organic phase of the hydrolyzed reaction sample after 20 h at 65° C. showed the presence of 1.59 mmol (80% yield) of 4-(1-hexynyl)-1,1'-biphenyl and no remaining 4-biphenylcarbonitrile in the reaction mixture.

EXAMPLE 40

This example illustrates the preparation of 3,3-dimethyl-1-butynylbenzene by a nickel catalyzed coupling of benzonitrile with 3,3-dimethyl-1-butynylzinc bromide (Table 1, entry 21).

The procedure was identical to Example 1, with the exception that 3,3-dimethyl-1-butyne (0.488 ml; 0.329 g; 4.00 mmol) was used as a substrate instead of phenylacetylene. GC analysis of the organic phase of the hydrolyzed reaction sample after 16 h at 65° C. showed the presence of 1.96 mmol (98% yield) of 3,3-dimethyl-1-butynylbenzene and no remaining benzonitrile in the reaction mixture.

EXAMPLE 41

This example illustrates the preparation of 2-(3,3-dimethyl-1-butynyl)furan by a nickel catalyzed coupling of 2-furonitrile with 3,3-dimethyl-1-butynylzinc bromide (Table 1, entry 22).

The procedure was identical to Example 1, with the exception that 3,3-dimethyl-1-butyne (0.488 ml; 0.329 g; 4.00 mmol) was used as a substrate instead of phenylacetylene and 2-furonitrile (0.175 ml; 0.186 g; 2.00 mmol) was used as a substrate instead of benzonitrile. GC analysis of the organic phase of the hydrolyzed reaction sample after 16 h at 65° C. showed the presence of 1.82 mmol (91% yield) of 2-(3,3-dimethyl-1-butynyl)furan and no remaining 2-furonitrile in the reaction mixture.

EXAMPLE 42

This example illustrates the preparation of 3-methoxy-1-(3,3-dimethyl-1-butynyl)benzene by a nickel catalyzed coupling of 3-methoxybenzonitrile with 3,3-dimethyl-1-butynylzinc bromide (Table 1, entry 23).

The procedure was identical to Example 1, with the exception that 3,3-dimethyl-1-butyne (0.488 ml; 0.329 g; 4.00 mmol) was used as a substrate instead of phenylacetylene and 3-methoxybenzonitrile (0.245 ml; 0.266 g; 2.00 mmol) was used as a substrate instead of benzonitrile. GC analysis of the organic phase of the hydrolyzed reaction sample after 16 h at 65° C. showed the presence of 1.85 mmol (92% yield) of 1-methoxy-3-(3,3-dimethyl-1-butynyl)benzene and no remaining 3-methoxybenzonitrile in the reaction mixture.

EXAMPLE 43

This example illustrates the preparation of 1-amino-3-(3,3-dimethyl-1-butynyl)benzene by a nickel catalyzed coupling of 3-aminobenzonitrile with 3,3-dimethyl-1-butynylzinc bromide using 5% catalyst loading (Table 1, entry 24).

The procedure was identical to Example 2, with the exception that 3,3-dimethyl-1-butyne (0.488 ml; 0.329 g; 4.00 mmol) was used as a substrate instead of phenylacetylene and 3-aminobenzonitrile (0.236 g; 2.00 mmol) was used as a substrate instead of benzonitrile. GC analysis of the organic phase of the hydrolyzed reaction sample after 45 h at 65° C. showed the presence of 0.96 mmol (48% yield) of 1-amino-3-(3,3-dimethyl-1-butynyl)benzene and 1.00 mmol of 3-aminobenzonitrile remaining in the reaction mixture.

EXAMPLE 44

This example illustrates the preparation of trimethyl(phenylethynyl)silane by a nickel catalyzed coupling of benzonitrile with trimethylsilylethynylzinc bromide (Table 1, entry 25).

The procedure was identical to Example 1, with the exception that trimethylsilylacetylene (0.565 ml; 0.393 g; 4.00 mmol) was used as a substrate instead of phenylacetylene. GC analysis of the organic phase of the hydrolyzed reaction sample after 23 h at 65° C. showed the presence of 1.74 mmol (87% yield) of trimethyl(phenylethynyl)silane, and no remaining benzonitrile in the reaction mixture.

EXAMPLE 45

This example illustrates the preparation of 4-(trimethylsilylethynyl)pyridine by a nickel catalyzed coupling of 4-cyanopyridine with trimethylsilylethynylzinc bromide (Table 1, entry 26).

The procedure was identical to Example 1, with the exception that 4-cyanopyridine (0.208 g; 2.00 mmol) was used as a substrate instead of benzonitrile and lithium trimethylacetylide (8.00 ml; 4.00 mmol; 0.5 M in THF) was used instead of the in situ derived lithium acetylide made from trimethylsilylacetylene and n-butyllithium. GC analysis of the organic phase of the hydrolyzed reaction sample after 20 h at 65° C. showed the presence of 1.12 mmol (56% yield) of 4-(trimethylsilylethynyl)pyridine and no remaining 3-cyanopyridine in the reaction mixture.

EXAMPLE 46

This example illustrates the preparation of 3-(trimethylsilylethynyl)pyridine by a nickel catalyzed coupling of 3-cyanopyridine with trimethylsilylethynylzinc bromide (Table 1, entry 27).

The procedure was identical to Example 1, with the exception that 3-cyanopyridine (0.208 g; 2.00 mmol) was used as a substrate instead of benzonitrile and lithium trimethylacetylide (8.00 ml; 4.00 mmol; 0.5 M in THF) was used instead of the in situ derived lithium acetylide made from trimethylsilylacetylene and n-butyllithium. GC analysis of the organic phase of the hydrolyzed reaction sample after 20 h at 65° C. showed the presence of 1.00 mmol (50% yield) of 3-(trimethylsilylethynyl)pyridine and no remaining 3-cyanopyridine in the reaction mixture.

EXAMPLE 47

This example illustrates the preparation of 1-methyl-4-(phenylethynyl)benzene by a nickel catalyzed coupling of benzonitrile with 4-methylphenylethynylzinc bromide (Table 1, entry 28).

The procedure was identical to Example 1, with the exception that 4-ethynyltoluene (0.507 ml; 0.465 g; 4.00 mmol) was used as a substrate instead of phenylacetylene. GC analysis of the organic phase of the hydrolyzed reaction sample after 42 h at 65° C. showed the presence of 1.62 mmol (81% yield) of 1-methyl-4-(phenylethynyl)benzene, and 0.25 mmol of benzonitrile remaining in the reaction mixture.

EXAMPLE 48

This example illustrates the preparation of 3-(4-methyl-1-phenylethynyl)pyridine by a nickel catalyzed coupling of 3-cyanopyridine with 4-methylphenylethynylzinc bromide (Table 1, entry 29).

The procedure was identical to Example 1, with the exception that 4-ethynyltoluene (0.507 ml; 0.465 g; 4.00 mmol) was used as a substrate instead of phenylacetylene and 3-cyanopyridine (0.208 g; 2.00 mmol) was used as a substrate instead of benzonitrile. GC analysis of the organic phase of the hydrolyzed reaction sample after 18 h at 65° C. showed the presence of 1.50 mmol (75% yield) of 3-(4-methyl-1-phenylethynyl)pyridine, and no remaining benzonitrile in the reaction mixture.

TABLE 1

Synthesis of Arylacetylenes via Ni-Catalyzed Coupling of Benzonitriles with Zinc Acetylides

| Entry | RZnBr | ArCN | Reaction Time (h) | Ar—R Product | Ar—R Yield (%) |
|---|---|---|---|---|---|
| 1 | Ph—C≡C—ZnBr | Ph—CN | 41 | Ph—C≡C—Ph | 79 |
| 2 | | Cl—C6H4—CN | 18 | Cl—C6H4—C≡C—Ph | 55 |
| | | | | Ph—C≡C—C6H4—C≡C—Ph | 4 |
| 3 | | 3-MeO—C6H4—CN | 40 | 3-MeO—C6H4—C≡C—Ph | 63 |

TABLE 1-continued
Synthesis of Arylacetylenes via Ni-Catalyzed Coupling of Benzonitriles with Zinc Acetylides
| Entry | RZnBr | ArCN | Reaction Time (h) | Ar—R Product | Ar—R Yield (%) |
|---|---|---|---|---|---|
| 4 | |  | 18 | 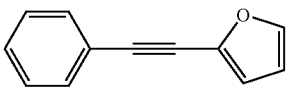 | 74 |
| 5 | | 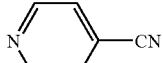 | 20 | 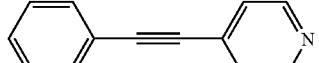 | 44[b] |
| 6 | | 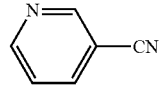 | 20 | 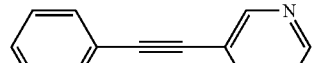 | 45[b] |
| 7 | | 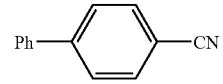 | 40 | 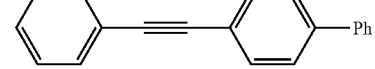 | 90 |
| 8 | CH$_3$(CH$_2$)$_5$—≡—ZnBr | 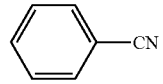 | 18 | 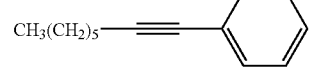 | 80 |
| 9 | |  | 23 | 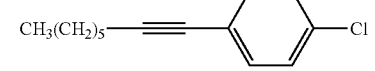 | 70 |
| | | | | 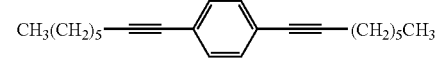 | 6 |
| 10 | |  | 46 |  | 83 |
| 11 | |  | 22 | 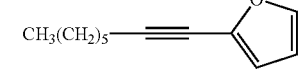 | 62[b] |
| 12 | | 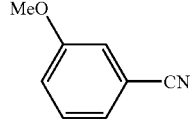 | 17 | 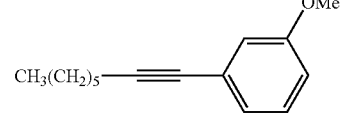 | 80 |
| 13 | | 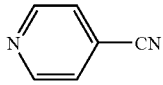 | 21 | 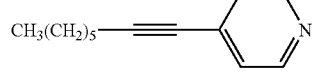 | 80[b,c] |
| 14 | |  | 45 | 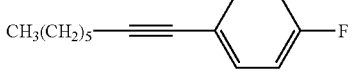 | 67[b] |
| 15 | | 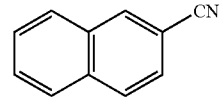 | 22 | 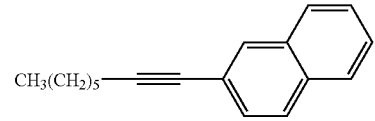 | 98[b] |
| 16 | CH$_3$(CH$_2$)$_3$—≡—ZnBr | 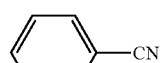 | 20 | 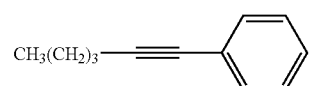 | 95 |

TABLE 1-continued

Synthesis of Arylacetylenes via Ni-Catalyzed Coupling of Benzonitriles with Zinc Acetylides

| Entry | RZnBr | ArCN | Reaction Time (h) | Ar—R Product | Ar—R Yield (%) |
|---|---|---|---|---|---|
| 17 | | 4-Cl-C6H4-CN | 20 | CH3(CH2)3-C≡C-C6H4-Cl | 65[b] |
| | | | | CH3(CH2)3-C≡C-C6H4-C≡C-(CH2)3CH3 | 5[b] |
| 18 | | 2-furyl-CN | 4 | CH3(CH2)3-C≡C-(2-furyl) | 69 |
| 19 | | 3-MeO-C6H4-CN | 20 | CH3(CH2)3-C≡C-C6H4-OMe | 74 |
| 20 | | 4-Ph-C6H4-CN | 20 | CH3(CH2)3-C≡C-C6H4-Ph | 80 |
| 21 | t-Bu-C≡C-ZnBr | PhCN | 16 | t-Bu-C≡C-Ph | 98 |
| 22 | | 2-furyl-CN | 16 | t-Bu-C≡C-(2-furyl) | 91 |
| 23 | | 3-MeO-C6H4-CN | 16 | t-Bu-C≡C-C6H4-OMe | 92 |
| 24 | | 3-H2N-C6H4-CN | 45 | t-Bu-C≡C-C6H4-NH2 | 48[b] |
| 25 | (H3C)3Si-C≡C-ZnBr | PhCN | 23 | (CH3)3Si-C≡C-Ph | 87 |
| 26 | | 4-pyridyl-CN | 20 | (CH3)3Si-C≡C-(4-pyridyl) | 56 |
| 27 | | 3-pyridyl-CN | 20 | (CH3)3Si-C≡C-(3-pyridyl) | 50 |
| 28 | 4-Me-C6H4-C≡C-ZnBr | PhCN | 42 | 4-Me-C6H4-C≡C-Ph | 81 |

TABLE 1-continued

Synthesis of Arylacetylenes via Ni-Catalyzed Coupling of Benzonitriles with Zinc Acetylides

| Entry | RZnBr | ArCN | Reaction Time (h) | Ar—R Product | Ar—R Yield (%) |
|---|---|---|---|---|---|
| 29 | | (3-pyridyl)CN | 18 | 4-methylphenyl—C≡C—(3-pyridyl) | 75 |

[a] All reactions were carried out with stoichiometries, catalyst loadings, etc., as illustrated in the representative procedure.
[b] 5% catalyst loading.
[c] The reaction was carried out at 23° C.

It is understood that the examples and embodiments described herein are for illustrative purposes only and that various modifications or changes in light thereof will be suggested to persons skilled in the art and are to be included within the spirit and purview of this application and scope of the appended claims.

All publications, patents, and patent applications cited herein are hereby incorporated by reference in their entirety for all purposes.

What is claimed is:

1. A process for the production of an acetylene compound having the formula Ar—C≡CR comprising reacting an aryl nitrile having the formula Ar—CN with an alkynylzinc or alkynylmagnesium compound having the formula RC≡C—M—X, or with a bis-alkynylzinc compound having the formula RC≡C—Zn—C≡CR, in the presence of a catalyst comprising nickel and a phosphine ligand having the formula $CH_3P(R_2)(R_3)$ in which $R_2$ and $R_3$ may be the same or different and are selected from $C_1$–$C_{12}$ alkyl, $C_1$–$C_{12}$ alkoxy, aryl, and aryloxy, wherein Ar represents an optionally substituted aromatic moiety; R represents hydrogen, an optionally substituted aromatic moiety, an optionally substituted aliphatic moiety, or a silyl group; M represents zinc or magnesium; and X represents Cl, Br, I, a catecholate group, or a group —OR, or —$SR_1$ in which $R_1$ represents optionally substituted $C_1$–$C_8$ alkyl, optionally substituted aryl, or optionally substituted aryl($C_1$–$C_8$)alkyl.

2. A process according to claim 1, in which Ar represents an optionally substituted hydrocarbyl aromatic moiety.

3. A process according to claim 1, in which Ar represents an optionally substituted phenyl or naphthyl moiety.

4. A process according to claim 1, in which Ar represents an unsubstituted hydrocarbyl aromatic moiety.

5. A process according to claim 1 in which Ar represents an unsubstituted phenyl or naphthyl moiety.

6. A process according to claim 1 in which Ar represents a substituted hydrocarbyl aromatic moiety.

7. A process according to claim 1 in which Ar represents a substituted phenyl or naphthyl moiety.

8. A process according to claim 1 in which Ar represents a phenyl or naphthyl moiety substituted by one or more groups selected from halogen, hydroxy, alkoxy, substituted alkoxy, optionally substituted alkyl, phenyl, amino, amide, ester moieties and carbonyl moieties.

9. A process according to claim 1 in which Ar represents an optionally substituted heterocyclic aromatic moiety.

10. A process according to claim 1 in which Ar represents an optionally substituted pyridyl, furyl, thienyl or pyrazolyl moiety.

11. A process according to claim 1 in which Ar represents an unsubstituted heterocyclic aromatic moiety.

12. A process according to claim 1 in which Ar represents an unsubstituted pyridyl, furyl, thienyl or pyrazolyl moiety.

13. A process according to claim 1 in which Ar represents a substituted heterocyclic aromatic moiety.

14. A process according to claim 1 in which Ar represents a substituted pyridyl, furyl, thienyl or pyrazolyl moiety.

15. A process according to claim 1 in which Ar represents a pyridyl or furyl moiety substituted by one or more groups selected from halogen, hydroxy, optionally substituted lower alkoxy, optionally substituted lower alkyl, phenyl, amino, amide, ester moieties or carbonyl moieties.

16. A process according to claim 1 in which R represents an optionally substituted aromatic moiety.

17. A process according to claim 1, in which R represents an optionally substituted hydrocarbyl aromatic moiety.

18. A process according to claim 1, in which R represents an optionally substituted phenyl or naphthyl moiety.

19. A process according to claim 1, in which R represents an unsubstituted hydrocarbyl aromatic moiety.

20. A process according to claim 1 in which R represents an unsubstituted phenyl or naphthyl moiety.

21. A process according to claim 1 in which R represents a substituted hydrocarbyl aromatic moiety.

22. A process according to claim 1 in which R represents a substituted phenyl or naphthyl moiety.

23. A process according to claim 1 in which R represents a phenyl or naphthyl moiety substituted by one or more groups selected from halogen, hydroxy, optionally substituted alkoxy, optionally substituted alkyl, phenyl, and amino moieties.

24. A process according to claim 1 in which R represents an optionally substituted heterocyclic aromatic moiety.

25. A process according to claim 1 in which R represents an optionally substituted pyridyl or furyl moiety.

26. A process according to claim 1 in which R represents an unsubstituted heterocyclic aromatic moiety.

27. A process according to claim 1 in which R represents an unsubstituted pyridyl or furyl moiety.

28. A process according to claim 1 in which R represents a substituted heterocyclic aromatic moiety.

29. A process according to claim 1 in which R represents a substituted pyridyl or furyl moiety.

30. A process according to claim 1 in which R represents a pyridyl or furyl moiety substituted by one or more groups selected from halogen, hydroxy, optionally substituted lower alkoxy, optionally substituted lower alkyl, phenyl, amino, amide, ester moieties and carbonyl moieties.

31. A process according to claim 1 in which Ar and R represent identical aromatic moieties.

32. A process according to claim 1 in which Ar and R represent different aromatic moieties.

33. A process according to claim 32 in which Ar represents an optionally substituted heterocyclic aromatic moiety and R represents an optionally substituted hydrocarbyl aromatic moiety.

34. A process according to claim 33 in which Ar represents an optionally substituted pyridyl or furyl moiety and R represents an optionally substituted phenyl or naphthyl moiety.

35. A process according to claim 34 in which Ar represents an optionally substituted pyridyl moiety and R represents an optionally substituted phenyl moiety.

36. A process according to claim 34 in which Ar represents an optionally substituted furyl moiety and R represents an optionally substituted phenyl moiety.

37. A process according to claim 1 in which R represents an optionally substituted aliphatic moiety.

38. A process according to claim 1 in which R represents an optionally subtitled saturated aliphatic moiety.

39. A process according to claim 1 in which R represents an optionally substituted saturated aliphatic moiety having from 1 to 10 carbon atoms.

40. A process according to claim 1 in which R represents an n-hexyl moiety.

41. A process according to claim 1 in which R represents an n-butyl moiety.

42. A process according to claim 1 in which R represents a tertiary butyl moiety.

43. A process according to claim 1 in which R represents a saturated aliphatic moiety substituted by a hydrocarbyl or heterocyclic aromatic moiety.

44. A process according to claim 1 in which R represents a silyl moiety having the formula $R_a R_b R_c Si$— in which $R_a$, $R_b$ and $R_c$ are independently hydrogen or optionally substituted aliphatic or aryl moieties.

45. A process according to claim 44 in which two of $R_a$, $R_b$ and $R_c$ are other than hydrogen.

46. A process according to claim 44 in which none of $R_a$, $R_b$ and $R_c$ is hydrogen.

47. A process according to claim 1 in which R represents a trimethylsilyl moiety.

48. A process according to claim 1 in which R is hydrogen.

49. A process according to claim 1 in which the aromatic nitrile is reacted with a compound having the formula RC≡C—M—X.

50. A process according to claim 49 in which M is zinc.

51. A process according to claim 50 in which X is Br or Cl.

52. A process according to claim 50 in which R is an optionally substituted aromatic moiety.

53. A process according to claim 50 in which R is an optionally substituted aliphatic moiety.

54. A process according to claim 50 in which R is a silyl moiety.

55. A process according to claim 50 in which the compound RC≡C—M—X is prepared by contacting an alkyllithium compound with a compound having the formula RC≡CH, and then contacting the resulting product with a zinc compound.

56. A process according to claim 49 in which M is magnesium.

57. A process according to claim 56 in which X is Br or Cl.

58. A process according to claim 56 in which R is an optionally substituted aromatic moiety.

59. A process according to claim 56 in which R is an optionally substituted aliphatic moiety.

60. A process according to claim 56 in which R is a silyl moiety.

61. A process according to claim 1 in which the aromatic nitrile is reacted with a bis-alkynyl zinc compound.

62. A process according to claim 1 in which the catalyst is formed in a previous step and is then contacted with the reactants.

63. A process according to claim 1 in which the catalyst is formed in situ from a nickel compound and a phosphine.

64. A process according to claim 1 in which the catalyst comprises a trimethylphosphine ligand.

65. A process according to claim 1 in which the catalyst comprises a dichlorobis(trimethylphosphine) ligand.

66. A process according to claim 1 in which the catalyst is present in an amount of from about 1 to about 25 mole %, based on the aryl nitrile.

67. A process according to claim 1 in which the catalyst is present in an amount of from about 5 to about 10 mole %, based on the aryl nitrile.

68. A process according to claim 1 in which the catalyst is present in an amount of about 5 mole %, based on the aryl nitrile.

69. A process according to claim 1 in which the catalyst is present in an amount of about 10 mole %, based on the aryl nitrile.

70. A process according to claim 1 further comprising contacting the reactants and catalyst with a diamine activator.

71. A process according to claim 32 in which the diamine activator is selected from N,N,N',N'-tetramethylethylenediamine and N,N,N',N'-tetramethyl-1,4-butanediamine.

72. A process according to claim 1 in which the ratio of the phosphine ligand to nickel is from about 1:1 to about 4:1.

73. A process according to claim 1 in which the ratio of the phosphine ligand to nickel is about 2:1.

74. A process according to claim 1 in which the temperature is from about to about 100° C.

75. A process according to claim 1 in which the temperature is from about 35 to about 70° C.

76. A process according to claim 1 conducted in the presence of a solvent system.

77. A process according to claim 32 in which the solvent system comprises tetrahydrofuran, 2-methyltetrahydrofuran, 1,3-dioxane, 1,4-dioxane, dimethylformamide, 1-methyl-2-pyrrolidinone, diglyme, toluene, or a mixture of two or more of the foregoing.

78. A process according to claim 32 in which the solvent system comprises tetrahydrofuran.

79. A process according to claim 1 in which Ar—CN is not 2-cyano-pyridine.

* * * * *

UNITED STATES PATENT AND TRADEMARK OFFICE
CERTIFICATE OF CORRECTION

| | | |
|---|---|---|
| PATENT NO. | : 7,105,707 B2 | Page 1 of 1 |
| APPLICATION NO. | : 10/740240 | |
| DATED | : September 12, 2006 | |
| INVENTOR(S) | : Joseph A. Miller et al. | |

It is certified that error appears in the above-identified patent and that said Letters Patent is hereby corrected as shown below:

Claim 71, line 1, delete the number "32" and replace it with -- 70 --.

Claim 77, line 1, delete the number "32" and replace it with -- 76 --.

Claim 78, line 1, delete the number "32" and replace it with -- 76 --.

Signed and Sealed this

First Day of May, 2007

JON W. DUDAS
*Director of the United States Patent and Trademark Office*